(12) United States Patent
Ingram et al.

(10) Patent No.: US 7,226,776 B2
(45) Date of Patent: Jun. 5, 2007

(54) RECOMBINANT HOSTS SUITABLE FOR SIMULTANEOUS SACCHARIFICATION AND FERMENTATION

(75) Inventors: Lonnie O'Neal Ingram, Gainesville, FL (US); Shengde Zhou, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 381 days.

(21) Appl. No.: 10/377,406

(22) Filed: Feb. 27, 2003

(65) Prior Publication Data

US 2004/0067555 A1    Apr. 8, 2004

Related U.S. Application Data

(63) Continuation of application No. 09/579,395, filed on May 26, 2000, now abandoned.

(60) Provisional application No. 60/136,376, filed on May 26, 1999.

(51) Int. Cl.
C07H 21/04     (2006.01)
C12N 1/12      (2006.01)

(52) U.S. Cl. .................. 435/252.1; 435/69.1; 435/183; 435/320.1; 435/325; 536/23.2; 536/23.4; 536/23.5; 536/23.6; 536/23.7; 536/24.1

(58) Field of Classification Search .............. 435/4, 435/6, 69.1, 183, 200, 210, 252.3, 320.1; 536/23.2; 530/350

See application file for complete search history.

(56) References Cited

U.S. PATENT DOCUMENTS

| | | | |
|---|---|---|---|
| 5,000,000 A | 3/1991 | Ingram et al. | 435/161 |
| 5,028,539 A | 7/1991 | Ingram et al. | 435/161 |
| 5,162,516 A | 11/1992 | Ingram et al. | 435/190 |
| 5,424,202 A | 6/1995 | Ingram et al. | 435/161 |
| 5,482,846 A | 1/1996 | Ingram et al. | 435/161 |
| 5,487,989 A | 1/1996 | Fowler et al. | 435/165 |
| 5,554,520 A | 9/1996 | Fowler et al. | 435/165 |
| 5,821,093 A | 10/1998 | Ingram et al. | 435/161 |

FOREIGN PATENT DOCUMENTS

WO    WO 98/45425    10/1998

OTHER PUBLICATIONS

Yoon et al. 1995, J. Microbiology (Seoul), vol. 33(2):126-127.*
Asghari et al., (1996) "Ethanol production from hemicellulose hydrolysates of agricultural residues using genetically engineered *Escherichia coli* strain KO11," *J. Ind. Microbiol.* 16:42-47.
Barbosa et al., (1992) "Expression of the *Zymomonas mobilis* alcohol dehydrogenase II (adhB) and pyruvate decarboxylase (pdc) genes in bacillus," *Current Microbiol.* 28:279-282.
Barras et al. (1994) "Extracellular enzymes and pathogenesis of soft-rot erwinia," *Annu. Rev. Phytopathol.* 32:201-234.

Beall et al. (1991) "Parametric studies of ethanol production from xylose and other sugars by recombinant *Escherichia coli*," *Biotechnol. Bioeng.* 38:296-303.
Beall et al., (1992) "Conversion of hydrolysates of corn cobs and hulls into ethanol by recombinant *Escherichia coli* B containing integrated genes for ethanol production," *Biotechnol. Lett.* 14:857-862.
Brau, B. et al. "Cloning and expression of the structural gene for pyruvate decarboxylase of *Zymomonas mobilis* in *Escherichia coli*" *Arch Microbiol.* 1986; 144:296-301.
Brooks et al., (1995) "Conversion of mixed waste office paper to ethanol by genetically engineered *Klebsiella oxytoca* strain P2," *Biotechnol. Progress.* 11:619-625.
Burchhardt et al., (1992), "Conversion of xylan to ethanol by ethanologenic strains of *Escherichia coli* and *Klebsiella oxytoca*," *Appl. Environ. Microbiol.* 58:1128-1133.
Conway et al., (1987), "Cloning and sequencing of the alcohol dehydrogenase II gene from *Zymomonas mobilis*," *J. Bacteriol.* 169:2591-2597.
Conway et al., (1987), "Gene expression in *Zymomonas mobilis*: promoter structure and identification of membrane anchor sequences forming functional lacZ' fusion proteins," *J. Bacteriol.* 169:2327-2335.
Curry, C. et al. "Expression and Secretion of a *Cellulomonas fimi* Exoglucanase in *Saccharomyces cerevisiae*" *Appl Environ Microbiol.* Feb. 1988, 54(2):476-484.
Doran et al., (1993) "Fermentation of crystalline cellulose to ethanol by *Klebsiella oxytoca* containing chromosomally integrated *Zymomonas mobilis* genes," *Biotechnol. Progress.* 9:533-538.
Doran et al., (1994) "Saccharification and fermentation of sugar cane bagasse by *Klebsiella oxytoca* P2 containing chromosomally integrated genes encoding the *Zymomonas mobilis* ethanol pathway," *Biotechnol. Bioeng.* 44:240-247.
Figurski et al., (1979) "Replication of a origin-containing derivative of plasmid RK2 dependent on a plasmid function provided in trans," *Proc. Natl. Acad. Sci. USA.* 76: 1648-1652.
Grepinet, O, et al. "Purification of *Clostridium thermocellum* xylanase Z expressed in *Escherichia coli* and identification of the corresponding product in the culture medium of *C. thermocellum.*" *J Bacteriol.* Oct. 1988;170(10):4576-81.

(Continued)

*Primary Examiner*—Manjunath N. Rao
(74) *Attorney, Agent, or Firm*—Edwards Angell Palmer & Dodge LLP; Peter C. Lauro, Esq.

(57) ABSTRACT

The invention provides recombinant host cells containing at least one heterologous polynucleotide encoding a polysaccharase under the transcriptional control of a surrogate promoter capable of increasing the expression of the polysaccharase. In addition, the invention further provides such hosts with genes encoding secretory protein/s to facilitate the secretion of the expressed polysaccharase. Preferred hosts of the invention are ethanologenic and capable of carrying out simultaneous saccharification fermentation resulting in the production of ethanol from complex cellulose substrates.

74 Claims, 8 Drawing Sheets

OTHER PUBLICATIONS

Grohmann et al., (1994) "Fermentation of galacturonic acid and other sugars in orange peel hydrolysates by the ethanologenic strain of *Escherichia coli*," *Biotechnol. Lett.* 16:281-286.

Guimaraes et al. , (1992) "Fermentation of sweet whey by ethanologenic *Escherichia coli*," *Biotechnol. Bioeng.* 40:41-45.

Guimaraes et al., (1992) Ethanol production from starch by recombinant *Escherichia coli* containing integrated genes for ethanol production and plasmid genes for saccharification, *Biotechnol. Lett.* 14:415-420.

Guiseppi et al., (1991), "Sequence analysis of the cellulase-encoding celY gene of *Erwinia chrysanthemi*: a possible case of interspecies gene transfer," *Gene* 106:109-114.

Hahn-Hagerdal et al., (1994) "An interlaboratory comparison of the performance of ethanol-producing micro-organism in a xylose-rich acid hydrolysate," *Appl. Microbiol. Biotechnol.* 41:62-72.

Hamilton et al., (1989), "New method for generating deletions and gene replacements in *Escherichia coli*," *J. Bacteriol.* 171:4617-4622.

He et al., (1991), "Cloned *Erwinia chrysanthemi* out genes enable *Escherichia coli* to selectively secrete a diverse family of heterologous proteins to its milieu," *Proc. Natl. Acad. Sci. USA*, 88:1079-1083.

Ingram, LO, et al. "Genetic engineering of ethanol production in *Escherichia coli*," *Appl Environ Microbiol*. Oct. 1987;53(10):2420-5.

Ingram et al., (1988) "Expression of different levels of ethanologenic enzymes from *Zymomonas mobilis* in recombinant strains of *Escherichia coli*," *Appl. Environ. Micrbiol.* 54:397-404.

Joliff, G. et al., "Isolation, Crystallization And Properties Of A New Cellulase Of *Clostridium thermocellum* Overproduced In *Escherichia coli*" *Bio/Technology*. Oct. 1986; 4: 896-900.

Kuhnert et al., (1997), "Detection system for *Escherichia coli*-specific virulence genes: absence of virulence determinants in B and C strains," *Appl. Environ. Microbiol.* 63:703-709.

Lai et al., (1996), "Cloning of cellobiose phosphoenolpyruvate-dependent phosphotransferase genes: functional expression in recombinant *Escherichia coli* and identification of a putative binding region for disaccharides," *Appl. Environ. Microbiol.* 63:355-363.

Lindeberg et al., (1992), "Analysis of eight out genes in a cluster required for pectic enzyme secretion by *Erwinia chrysanthemi*: sequence comparison with secretion genes from other gram-negative bacteria," *J. of Bacteriology* 174:7385-7397.

Lindeberg et al., (1996), "Complementation of deletion mutations in a cloned functional cluster of *Erwinia chrysanthemi* out genes with *Erwinia carotovora* out homologues reveals OutC and OutD as candidate gatekeepers of species-specific secretion of proteins via the type II pathway," *Mol. Micro.* 20:175-190.

Moniruzzaman et al., (1996) "Ethanol production from afex pretreated corn fiber by recombinant bacteria," *Biotechnol. Lett.* 18:955-990.

Moniruzzaman et al. (1997), "Extracellular melibiose and fructose are intermediates in raffinose catabolism during fermentation to ethanol by engineered enteric bacteria," *J. Bacteriol.* 179:1880-1886.

Moniruzzaman et al., (1997), "Isolation and molecular characterization of high-performance cellobiose-fermenting spontaneous mutants of ethanologenic *Escherichia coli* KO11 containing the *Klebsiella oxytoca* casAB operon," *Appl. Environ. Microbiol.* 63:4633-4637.

Moniruzzaman et al., (1998) "Ethanol production from dilute acid hydrolysate of rice hulls using genetically engineered *Escherichia coli*," *Biotechnol. Lett.* 20:943-947.

Murata et al., (1990), "Characterization of transposon insertion out-mutants of *Erwinia carotovora* subsp. carotovora defective in enzyme export and of a DNA segment that complements out mutations in *E. carotovora* subsp. carotovora, *E. carotovora* subsp. atroseptica, and *Erwinia chrysanthemi*," *J. Bacteriol.* 172:2970-2978.

Neale, AD. et al. "Nucleotide sequence of the pyruvate decarboxylase gene from *Zymomonas mobilis*." *Nucleic Acids Res.* Feb. 25, 1987;15(4):1753-61.

Ohta et al., (1991), "Genetic improvement of *Escherichia coli* for ethanol production: chromosomal integration of *Zymomonas mobilis* genes encoding pyruvate decarboxylase and alcohol dehydrogenase II," *Appl. Environ. Microbiol.* 57:893-900.

Posfai et al., (1997), "Versatile insertion plasmids for targeted genome manipulations in bacteria: isolation, deletion, and rescue of the pathogenicity island LEE of the *Escherichia coli* O157:H7 genome," *J. Bacteriol.* 179:4426-4428.

Pugsley (1993), "The complete general secretory pathway in gram-negative bacteria," *Microbiol. Rev.* 57:50-108.

Pugsley, A. P. et al., "Secretion of the cell surface lipoprotein pullulanase in *Escherichia coli*," *J. Biological Chem.*, 266(21):13640-13645 (1991).

Py et al., (1991), "Cellulase EGZ of *Erwinia chrysanthemi*: structural organization and importance of His98 and Glu133 residues for catalysis," *Protein Engineering* 4:325-333.

Py et al. (1991) "Secretion of cellulases in *Erwinia chrysanthemi* and *E. carotovora* is species-specific," *FEMS Microbiol. Lett.* 79:315-322.

Sauvonnet et al. (1996), "Identification of two regions of *Klebsiella oxytoca* pullulanase that together are capable of promoting beta-lactamase secretion by the general secretory pathway," *Mol. Micrbiol.* 22: 1-7.

Tolan, JS et al. "Fermentation of D-Xylose and L-Arabinose to Ethanol by *Erwinia chrysanthemi*" *Appl Environ Microbiol*. Sep. 1987; 53(9):2033-2038.

Tolan, JS et al. "Fermentation of D-Xylose to Ethanol by Genetically Modified *Klebsiella planticola*" *Appl Environ Microbiol*. Sep. 1987; 53(9):2039-2044.

Vroeman et al., (1995), "Cloning and characterization of the bgxA gene from *Erwinia chrysanthemi* D1 which encodes a beta-glucosidase/xylosidase enzyme," *Mol. Gen. Genet.* 246:465-477.

Wang et al., (1989), "Multiple in vivo roles for the -12-region elements of sigma 54 promoters," *J. Bacteriol.* 180:5626-5631.

Wise et al., (1996), "Sequences in the -35 region of *Escherichia coli* rpoS-dependent genes promote transcription by E sigma S," *J. Bacteriol.* 178:2785-2793.

Wood et al. (1988), "Biomass. Part A. Cellulose and hemicellulose," *Methods in Enzymology* 160: 87-112.

Wood et al., (1992), "Ethanol production from cellobiose, amorphous cellulose, and crystalline cellulose by recombinant *Klebsiella oxytoca* containing chromosomally integrated *Zymomonas mobilis* genes for ethanol production and plasmids expressing thermostable cellulase genes from *Clostridium thermocellum*," *Appl. Environ. Microbiol.* 58:2103-2110.

Wood et al., (1997) "Production of recombinant bacterial endoglucanase as a co-product with ethanol during fermentation using derivatives of *Escherichia coli* KO11," *Biotech. Bioeng.* 55:547-555.

Yomano et al., (1998) "Isolation and characterization of ethanol-tolerant mutants of *Escherichia coli* KO11 for fuel ethanol production," *J. of Ind. Micro. & Bio.* 20:132-138.

Zhou, S. et al., "Enhancement of expression and apparent secretion of *Erwinia chrysanthemi* endoglucanase (encoded by celZ) in *Escherichia coli* B," *Appl. Environ. Microbiol.* 65(6):2439-2445 (1999).

Pugsley, A.P. et al., "Secretion of the cell surface lipoprotein pullulanase in *Escherichia coli*",*J. Biological Chem.*, 266(21):13640-13645 (1991)

Zhou, S. et al.,"Engineering endoglucanase-secreting strains of ethanologenic *Klebsiella oxytoca* P2", J. of Ind. Microbiol. And Technol.: 22(6) 600-607 (1999).

\* cited by examiner

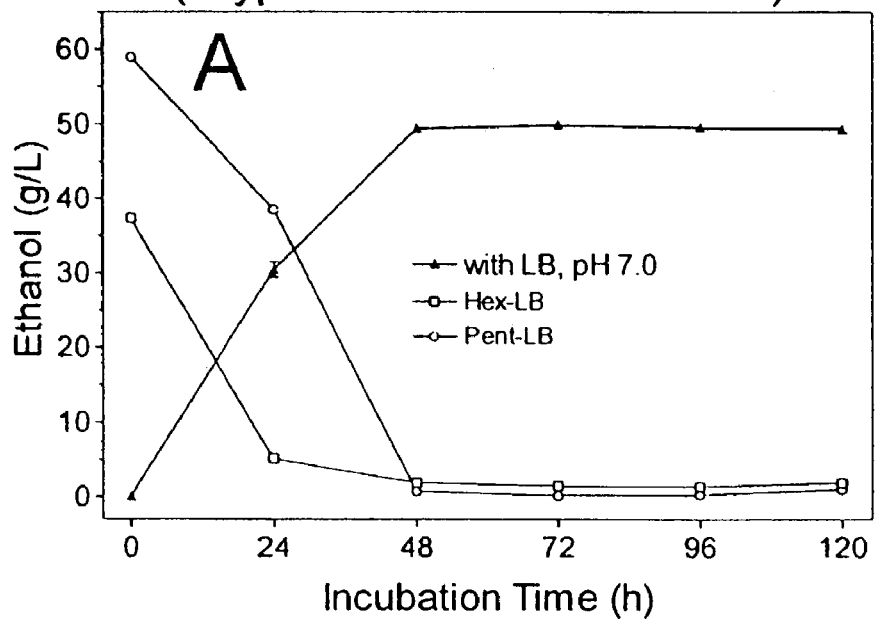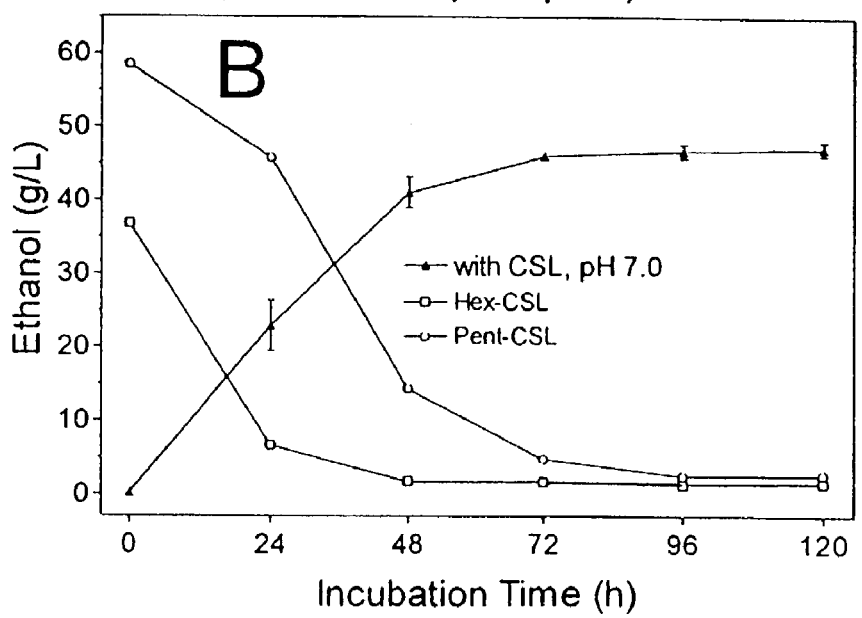
Fig. 1

```
                      -35 region                         -10 region              #
1051 CTTTTTCGGC ATGAGCAACC AACATTTTCA AGGTATCATC CTGATGCGCA 1101 ATATCGGCAT CGGTTAGCCA TAACCATTTT ACCTGTCCGG CGGCCTTAAT
1151 ACCTTGATCA GATGGTTCGT GGTGTTGTTA CCTTGCCGAA GGGCACCGGT
1201 AAAAATGTTC GCGTCGGTGT TTCGCCCGT GGCCCGAAAG CTGAAGAAGC
1251 TAAAGCTGCT GGTGCAGAAG TTGTCGGGCG AGAAGACCTG ATGGAAGCCA
                      -35 region                               -10 region
1301 TTCAGGGGCGG CAGCATTGAT TTCGATCGTG ATGCCCTTTA TACTGAAATT
      #
1351 GCCTTGCCGCT GCCATAATGA AGCAGCCTCC GGTGTTTTGG CAGATTTAAG
                                      Shine-Dalgarno
1401 CGCTGCCTGA TTTTCGTgat cctctagagt ctatgaaatg gagattcatt celZ coding region-->
1451 tatgcctctc tcttattcgg ataaccatcc agtcatccgc aagcttggcc
```

*Fig. 5* pLOI2306 (11520 bps)

RECOMBINANT HOSTS SUITABLE FOR SIMULTANEOUS SACCHARIFICATION AND FERMENTATION

RELATED INFORMATION

This application is a continuation of U.S. application Ser. No. 09/579,395, filed on May 26, 2000, now abandoned, which claims priority to U.S. provisional Application No. 60/136,376, entitled "RECOMBINANT HOSTS SUITABLE FOR SIMULTANEOUS SACCHARIFICATION AND FERMENTATION," filed on May 26, 1999, incorporated herein in its entirety by this reference. The contents of all patents, patent applications, and references cited throughout this specification are hereby incorporated by reference in their entireties.

GOVERNMENT SPONSORED RESEARCH

This work was supported, in part, by grants from the United States Department of Agriculture, National Research Initiative (95-37308-1843; 98-35504-6177), and United States Department of Energy (DE-FG02-96ER20222). The Government has certain rights in the invention.

BACKGROUND OF THE INVENTION

Many environmental and societal benefits would result from the replacement of petroleum-based automotive fuels with renewable fuels obtained from plant materials (Lynd et al., (1991) *Science* 251:1318–1323; Olson et al., (1996) *Enzyme Microb. Technol.* 18:1–17; Wyman et al., (1995) *Amer. Chem. Soc. Symp.* 618:272–290). Each year, the United States burns over 120 billion gallons of automotive fuel, roughly equivalent to the total amount of imported petroleum. The development of ethanol as a renewable alternative fuel has the potential to eliminate United States dependence on imported oil, improve the environment, and provide new employment (Sheehan, (1994) ACS Symposium Series No. 566, ACS Press, pp 1–53).

In theory, the solution to the problem of imported oil for automotive fuel appears quite simple. Rather than using petroleum, a finite resource, the ethanol can be produced efficiently by the fermentation of plant material, a renewable resource. Indeed, Brazil has demonstrated the feasibility of producing ethanol and the use of ethanol as a primary automotive fuel for more than 20 years. Similarly, the United States produces over 1.2 billion gallons of fuel ethanol each year. Currently, fuel ethanol is produced from corn starch or cane syrup utilizing either *Saccharomyces cerevisiae* or *Zymomonas mobilis* (*Z. mobilis*). However, neither of these sugar sources can supply the volumes needed to realize a replacement of petroleum-based automotive fuels. In addition, both cane sugar and corn starch are relatively expensive starting materials which have competing uses as food products.

Moreover, these sugar substrates represent only a fraction of the total carbohydrates in plants. Indeed, the majority of the carbohydrates in plants is in the form of lignocellulose, a complex structural polymer containing cellulose, hemicellulose, pectin, and lignin. Lignocellulose is found in, for example, the stems, leaves, hulls, husks, and cobs of plants. Hydrolysis of these polymers releases a mixture of neutral sugars including glucose, xylose, mannose, galactose, and arabinose. No known natural organism can rapidly and efficiently metabolize all these sugars into ethanol.

Nonetheless, in an effort to exploit this substrate source, the Gulf Oil Company developed a method for the production of ethanol from cellulose using a yeast-based process termed simultaneous saccharification and fermentation (SSF) (Gauss et al. (1976) U.S. Pat. No. 3,990,944). Fungal cellulase preparations and yeasts were added to a slurry of the cellulosic substrate in a single vessel. Ethanol was produced concurrently during cellulose hydrolysis. However, Gulf's SSF process has some shortcomings. For example, fungal cellulases have been considered, thus far, to be too expensive for use in large scale bioethanol processes (Himmel et al., (1997) Amer. Chem. Soc. pp. 2–45; Ingram et al., (1987) *Appl. Environ. Microbiol.* 53:2420–2425; Okamoto et al., (1994) *Appl. Microbiol. Biotechnol.* 42:563–568; Philippidis, G., (1994) Amer. Chem. Soc. pp. 188–217; Saito et al., (1990) *J. Ferment. Bioeng.* 69:282–286; Sheehan, J., (1994) Amer. Chem. Soc. pp 1–52; Su et al., (1993) *Biotechnol. Lett.* 15:979–984).

SUMMARY OF THE INVENTION

The development of inexpensive enzymatic methods for cellulose hydrolysis has great potential for improving the efficiency of substrate utilization and the economics of the saccharification and fermentation process. Accordingly, developing a biocatalyst which can be used for the efficient depolymerization of a complex cellulosic substrate and subsequent rapid fermentation of the substrate into ethanol, would be of great benefit.

The present invention provides a recombinant host cell engineered for increased expression and secretion of a polysaccharase suitable for depolymerizing complex carbohydrates. Specifically exemplified are two recombinant enteric bacteria, *Escherichia coli* and *Klebsiella oxytoca*, which express a polysaccharase at high levels under the transcriptional control of a surrogate promoter. The invention provides for the further modification of these hosts to include a secretory protein/s which allows for the increased production of polysaccharase in cell. In a preferred embodiment, the polysaccharase is produced in either increased amounts, with increased activity, or a combination thereof. In a preferred embodiment, the invention provides for the further modification of these hosts to include exogenous ethanologenic genes derived from an efficient ethanol producer, such as *Zymomonas mobilis*. Accordingly, these hosts are capable of expressing high levels of proteins that may be used alone or in combination with other enzymes or recombinant hosts for the efficient production of ethanol from complex carbohydrates.

More particularly, in a first aspect, the present invention features a recombinant host cell having increased production of a polysaccharase. The host cell of this aspect contains a heterologous polynucleotide segment containing a sequence that encodes a polysaccharase where the sequence is under the transcriptional control of a surrogate promoter and this promoter is capable of causing increased production of the polysaccharase. In addition, this aspect features a host cell that also contains a second heterologous polynucleotide segment containing a sequence that encodes a secretory polypeptide. The expression of the first and second heterologous polynucleotide segments results in the increased production of polysaccharase amounts, activity, or a combination thereof, by the recombinant host cell.

In a preferred embodiment, the polysaccharase polypeptide is secreted.

In another embodiment, the host cell is a bacterial cell, preferably Gram-negative, facultatively anaerobic, and from the family Enterobacteriaceae. In another related embodiment, the recombinant host cell is of the genus *Escherichia* or *Klebsiella* and, preferably, is the strain *E. coli* B, *E. coli* DH5α, *E. coli* KO4 (ATCC 55123), *E. coli* KO11 (ATCC 55124), *E. coli* KO12 (ATCC 55125), *E. coli* LY01, *K. oxytoca* M5A1, or *K. oxytoca* P2 (ATCC 55307).

In another embodiment, the recombinant host contains a polynucleotide segment that encodes a polysaccharase that is a glucanase, endoglucanase, exoglucanase, cellobiohydrolase, β-glucosidase, endo-1,4-β-xylanase, α-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or may be a combination of these polysaccharases. In a related embodiment, the polysaccharase is preferably a glucanase, more preferably an expression product of a celZ gene, and most preferably, derived from *Erwinia chrysanthemi*.

In yet another embodiment, the recombinant host cell expresses a secretory polypeptide encoded by a pul or out gene preferably derived from a bacterial cell selected from the family Enterobacteriaceae and more preferably, from *K. oxytoca, E. carotovora, E. carotovora* subspecies *carotovora, E. carotovora* subspecies *atroseptica*, or *E. chrysanthemi*.

In a further embodiment, the surrogate promoter for driving gene expression in the recombinant host cell is derived from a polynucleotide fragment from *Zymomonas mobilis*, and more preferably, is the sequence provided in SEQ ID NO: 1, or a fragment of that sequence.

In even another embodiment, the host cell of the above aspect and foregoing embodiments is ethanologenic.

In a second aspect, the present invention provides a recombinant ethanologenic host cell containing a heterologous polynucleotide segment that encodes a polysaccharase and this segment is under the transcriptional control of an exogenous surrogate promoter.

In one embodiment, the host cell is a bacterial cell, preferably Gram-negative, facultatively anaerobic, and from the family Enterobacteriaceae. In a related embodiment, the recombinant ethanologenic host cell is of the genus *Escherichia* or *Klebsiella* and, preferably, is the strain *E. coli* B, *E. coli* DH5α, *E. coli* KO4 (ATCC 55123), *E. coli* KO11 (ATCC 55124), *E. coli* KO12 (ATCC 55125), *E. coli* LY01, *K. oxytoca* M5A1, or *K. oxytoca* P2 (ATCC 55307).

In another embodiment, the recombinant host cell contains a polynucleotide segment that encodes a polysaccharase that is a glucanase, endoglucanase, exoglucanase, cellobiohydrolase, α-glucosidase, endo-1,4-α-xylanase, β-xylosidase, β-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of these polysaccharases. In a related embodiment, the polysaccharase is a glucanase, preferably an expression product of a celZ gene, and more preferably, derived from *Erwinia chrysanthemi*.

In another embodiment, the surrogate promoter for driving gene expression in the recombinant host cell is derived from a polynucleotide fragment from *Zymomonas mobilis*, and more preferably, is the sequence provided in SEQ ID NO: 1, or is a fragment of that sequence.

In another preferred embodiment, the above aspect and foregoing embodiments features a host cell that is ethanologenic.

In a third aspect, the invention features a recombinant ethanologenic Gram-negative bacterial host cell containing a first heterologous polynucleotide segment containing a sequence encoding a first polypeptide and a second heterologous polynucleotide segment containing a sequence encoding a secretory polypeptide/s where the first heterologous polysaccharide is under the transcriptional control of a surrogate promoter and the production of the first polypeptide by the host cell is increased.

In one embodiment, the first polypeptide is secreted.

In another embodiment, the recombinant host cell is a facultatively anaerobic bacterial cell. In a related embodiment, the host cell is from the family Enterobacteriaceae, preferably *Escherichia* or *Klebsiella,* and more preferably, is the strain *E. coli* B, *E. coli* DH5α, *E. coli* KO4 (ATCC 55123), *E. coli* KO11 (ATCC 55124), *E. coli* KO12 (ATCC 55125), or *E. coli* LY01, *K. oxytoca* M5A1, or *K. oxytoca* P2 (ATCC 55307).

In another embodiment, the first polypeptide of the recombinant host is a polysaccharase, and, preferably the polypeptide is of increased activity. In a related embodiment, the polysaccharase is a glucanase, endoglucanase, exoglucanase, cellobiohydrolase, α-glucosidase, endo-1,4-α-xylanase, α-xylosidase, β-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of these polysaccharases.

In a preferred embodiment, the first polypeptide of the recombinant host is the polysaccharase glucanase, preferably an expression product of the celZ gene, and more preferably, is derived from *Erwinia chrysanthemi*.

In another embodiment, the second heterologous polynucleotide segment of the recombinant host cell contains at least one pul gene or out gene, preferably derived from a bacterial cell from the family Enterobacteriaceae and more preferably, from *K. oxytoca, E. carotovora, E. carotovora* subspecies *carotovora, E. carotovora* subspecies *atroseptica,* or *E. chrysanthemi*.

In a fourth aspect, the invention provides a method for enzymatically degrading an oligosaccharide. The method involves contacting an oligosaccharide with a host cell containing a first heterologous polynucleotide segment containing a sequence encoding a polysaccharase that is under the transcriptional control of a surrogate promoter. Moreover, the surrogate promoter is capable of causing increased production of the polysaccharase. In addition, the recombinant host cell of the above method also contains a second heterologous polynucleotide segment containing a sequence encoding a secretory polypeptide. The expression of the first and second polynucleotide segments of the host cell of this aspect result in the production of an increased amount of polysaccharase activity such that the oligosaccharide is enzymatically degraded. In a preferred embodiment, the polysaccharase is secreted.

In one embodiment of the above aspect, the host cell is ethanologenic. In another embodiment, the method is carried out in an aqueous solution. In even another embodiment, the method is used for simultaneous saccharification and fermentation. In still another embodiment, the oligosaccharide is preferably lignocellulose, hemicellulose, cellulose, pectin, or any combination of these oligosaccharides.

In a fifth aspect, the invention features a method of identifying a surrogate promoter capable of increasing the expression of a gene-of-interest in a host cell. The method involves fragmenting a genomic polynucleotide from an organism into one or more fragments and placing a gene-of-interest under the transcriptional control of at least one of these fragments. The method further involves introducing such a fragment and gene-of-interest into a host cell and identifying a host cell having increased production of the gene-of-interest such that the increased expression indicates that the fragment is a surrogate promoter.

In a sixth aspect, the invention provides a method of making a recombinant host cell for use in simultaneous saccharification and fermentation. In particular, the method involves introducing into the host cell a first heterologous polynucleotide segment containing a sequence encoding a polysaccharase polypeptide under the transcriptional control of a surrogate promoter, the promoter being capable of causing increased expression of the polysaccharase polypeptide. In addition, the method further includes introducing into the host cell a second heterologous polynucleotide segment containing a sequence encoding a secretory polypeptide/s such that the expression of the first and second polynucleotide segments results in the increased production of a polysaccharase polypeptide by the recombinant host cell. In a preferred embodiment, the increased production of the polysaccharase polypeptide is an increase in activity, amount, or a combination thereof. In another preferred embodiment, the polysaccharase polypeptide is secreted. In a more preferred embodiment, the host cell is ethanologenic.

In a seventh aspect, the invention features a vector comprising the sequence of pLOI2306 (SEQ ID NO: 12).

In an eighth aspect, the invention features a host cell comprising the foregoing vector.

In a ninth aspect, the invention features a method of making a recombinant host cell integrant including the steps of introducing into the host a vector comprising the sequence of pLOI2306 and identifying a host cell having the vector stably integrated.

In a tenth aspect, the invention features a method for expressing a polysaccharase in a host cell encompassing the steps of introducing into the host cell a vector containing the polynucleotide sequence of pLOI2306 and identifying a host cell expressing the polysaccharase. In a preferred embodiment, each of the above aspects features a host cell that is ethanologenic.

In an eleventh aspect, the invention provides a method for producing ethanol from an oligosaccharide source by contacting said oligosaccharide source with a ethanologenic host cell containing a first heterologous polynucleotide segment comprising a sequence encoding a polysaccharase under the transcriptional control of a surrogate promoter. Moreover, the promoter is capable of causing increased expression of the polysaccharase. In addition, the ethanologenic host contains a second heterologous polynucleotide segment comprising a sequence encoding a secretory polypeptide. The expression of said first and second polynucleotide segments of the ethanologenic host cell result in the increased production of polysaccharase activity by the host cell such that the oligosaccharide source is enzymatically degraded and fermented into ethanol.

In one embodiment, the first polypeptide of the recombinant host is a polysaccharase, and, preferably the polypeptide is of increased activity. In a related embodiment, the polysaccharase is a glucanase, endoglucanase, exoglucanase, cellobiohydrolase, α-glucosidase, endo-1,4-α-xylanase, β-xylosidase, β-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of these polysaccharases.

In a preferred embodiment, the first polypeptide of the recombinant host is the polysaccharase glucanase, preferably an expression product of the celZ gene, and more preferably, is derived from *Erwinia chrysanthemi*.

In another embodiment, the second heterologous polynucleotide segment of the recombinant host cell contains at least one pul gene or out gene, preferably derived from a bacterial cell from the family Enterobacteriaceae and more preferably, from *K. oxytoca, E. carotovora, E. carotovora* subspecies *carotovora, E. carotovora* subspecies *atroseptica*, or *E. chrysanthemi*.

In another embodiment, the recombinant host cell is a facultatively anaerobic bacterial cell. In a related embodiment, the host cell is from the family Enterobacteriaceae, preferably *Escherichia* or *Klebsiella,* and more preferably, is the strain *E. coli* KO4 (ATCC 55123), *E. coli* KO11 (ATCC 55124), *E. coli* KO12 (ATCC 55125), *K. oxytoca* M5A1, or *K. oxytoca* P2 (ATCC 55307).

In another embodiment, the method is carried out in an aqueous solution. In even another embodiment, the method is used for simultaneous saccharification and fermentation. In still another embodiment, the oligosaccharide is preferably lignocellulose, hemicellulose, cellulose, pectin, or any combination of these oligosaccharides.

In yet another embodiment, the method uses a nucleic acid construct that is, or is derived from, a plasmid selected from the group consisting of pLOI2306.

Other features and advantages of the invention will be apparent from the following detailed description and claims.

BRIEF DESCRIPTION OF THE DRAWINGS

FIG. 1 shows fermentation rates for the ethanologenic recombinant host *E. coli* KO11 using rice hull substrates pretreated with dilute acid and supplemented with two different medias.

FIG. 5 shows the partial nucleotide sequence (SEQ ID NO: 1) of the *Z. mobilis* DNA fragment in the pLOI2183 plasmid that functions as a surrogate promoter. The full sequence has been assigned GenBank accession number AF109242 (SEQ ID NO: 2). Indicated are two transcriptional start sites (#), −35 and −10 regions, the Shine-Delgarno site (bold), partial vector and celZ sequence (lowercase), and the celZ start codon (atg indicated in bold).

DETAILED DESCRIPTION OF THE INVENTION

Figure 2:
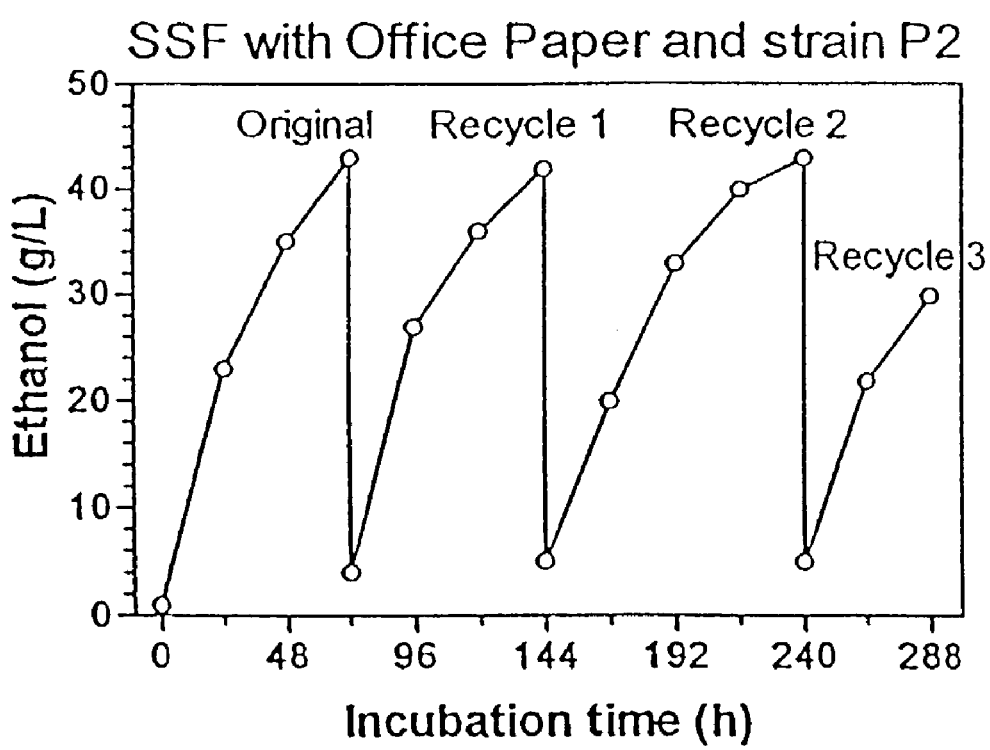
FIG. 2 shows simultaneous saccharification and fermentation (SSF) rates for the ethanologenic recombinant host strain *K. oxytoca* P2 using mixed waste office paper. Insoluble residues from SSF were recycled as a source of bound cellulase enzymes and substrate during subsequent fermentations.

In order for the full scope of the invention to be clearly understood, the following definitions are provided.

I. Definitions

As used herein the term "recombinant host" is intended to include a cell suitable for genetic manipulation, e.g., which can incorporate heterologous polynucleotide sequences, e.g., which can be transfected. The cell can be a microorganism or a higher eukaryotic cell. The term is intended to include progeny of the cell originally transfected. In preferred embodiments, the cell is a bacterial cell, e.g., a Gram-negative bacterial cell, and this term is intended to include all facultatively anaerobic Gram-negative cells of the family Enterobacteriaceae such as *Escherichia, Shigella, Citrobacter, Salmonella, Klebsiella, Enterobacter, Erwinia, Kluyvera, Serratia, Cedecea, Morganella, Hafnia, Edwardsiella, Providencia, Proteus*, and *Yersinia*. Particularly preferred recombinant hosts are *Escherichia coli* or *Klebsiella oxytoca* cells.

The term "heterologous polynucleotide segment" is intended to include a polynucleotide segment that encodes one or more polypeptides or portions or fragments of polypeptides. A heterologous polynucleotide segment may be derived from any source, e.g., eukaryotes, prokaryotes, virii, or synthetic polynucleotide fragments.

The terms "polysaccharase" or "cellulase" are used interchangeably herein and are intended to include a polypeptide capable of catalyzing the degradation or depolymerization of any linked sugar moiety, e.g., disaccharides, trisaccharides, oligosaccharides, including, complex carbohydrates, e.g., lignocellulose, which comprises cellulose, hemicellulose, and pectin. The terms are intended to include cellulases such as glucanases, including both endoglucanases and exoglucanases, and β-glucosidase. More particularly, the terms are intended to include, e.g., cellobiohydrolase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of any of these cellulases.

The term "surrogate promoter" is intended to include a polynucleotide segment that can transcriptionally control a gene-of-interest that it does not transcriptionally control in nature. In a preferred embodiment, the transcriptional control of a surrogate promoter results in an increase in expression of the gene-of-interest. In a preferred embodiment, a surrogate promoter is placed 5' to the gene-of-interest. A surrogate promoter may be used to replace the natural promoter, or may be used in addition to the natural promoter. A surrogate promoter may be endogenous with regard to the host cell in which it is used or it may be a heterologous polynucleotide sequence introduced into the host cell, e.g., exogenous with regard to the host cell in which it is used.

The terms "oligosaccharide source," "oligosaccharide," "complex cellulose," "complex carbohydrate," and "polysaccharide" are used essentially interchangeably and are intended to include any carbohydrate source comprising more than one sugar molecule. These carbohydrates may be derived from any unprocessed plant material or any processed plant material. Examples are wood, paper, pulp, plant derived fiber, or synthetic fiber comprising more than one linked carbohydrate moiety, i.e., one sugar residue. One particular oligosaccharide source is lignocellulose which represents approximately 90% of the dry weight of most plant material and contains carbohydrates, e.g., cellulose, hemicellulose, pectin, and aromatic polymers, e.g., lignin. Cellulose, makes up 30%–50% of the dry weight of lignocellulose and is a homopolymer of cellobiose (a dimer of glucose). Similarly, hemicellulose, makes up 20%–50% of the dry weight of lignocellulose and is a complex polymer containing a mixture of pentose (xylose, arabinose) and hexose (glucose, mannose, galactose) sugars which contain acetyl and glucuronyl side chains. Pectin makes up 1%–20% of the dry weight of lignocellulose and is a methylated homopolymer of glucuronic acid. Any one or a combination of the above carbohydrate polymers are potential sources of sugars for depolymerization and subsequent bioconversion to ethanol by fermentation according to the products and methods of the present invention.

The term "gene/s" is intended to include nucleic acid molecules, e.g., polynucleotides which include an open reading frame encoding a polypeptide, and can further include non-coding regulatory sequences, and introns. In addition, the term gene/s is intended to include one or more genes that map to a functional locus, e.g., the out or pul genes of *Erwinia* and *Klebsiella*, respectively, that encode more than one gene product, e.g., a secretory polypeptide.

The term "gene-of-interest" is intended to include a specific gene for a selected purpose. The gene may be endogenous to the host cell or may be recombinantly introduced into the host cell. In a preferred embodiment, a gene-of-interest is involved in at least one step in the bioconversion of a carbohydrate to ethanol. Accordingly, the term is intended to include any gene encoding a polypeptide such as an alcohol dehydrogenase, a pyruvate decarboxylase, a secretory protein/s, or a polysaccharase, e.g., a glucanase, such as an endoglucanase or exoglucanase, a cellobiohydrolase, β-glucosidase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

The term "fragmenting a genomic polynucleotide from an organism" is intended to include the disruption of the genomic polynucleotide belonging to an organism into one or more segments using either mechanical, e.g., shearing, sonication, trituration, or enzymatic methods, e.g., a nuclease. Preferably, a restriction enzyme is used in order to facilitate the cloning of genomic fragments into a test vector for subsequent identification as a candidate promoter element. A genomic polynucleotide may be derived from any source, e.g., eukaryotes, prokaryotes, virii, or synthetic polynucleotide fragments.

The term "simultaneous saccharification and fermentation" or "SSF" is intended to include the use of one or more recombinant hosts for the contemporaneous degradation or depolymerization of a complex sugar and bioconversion of that sugar residue into ethanol by fermentation.

The term "transcriptional control" is intended to include the ability to modulate gene expression at the level of transcription. In a preferred embodiment, transcription, and thus gene expression, is modulated by replacing or adding a surrogate promoter near the 5' end of the coding region of a gene-of-interest thereby resulting in altered gene expression.

The term "expression" is intended to include the expression of a gene at least at the level of RNA production.

The term "expression product" is intended to include the resultant product of an expressed gene, e.g., a polypeptide.

The term "increased expression" is intended to include an alteration in gene expression at least at the level of increased RNA production and preferably, at the level of polypeptide expression.

The term "increased production" is intended to include an increase in the amount of a polypeptide expressed, in the level of the enzymatic activity of the polypeptide, or a combination thereof.

The terms "activity" and "enzymatic activity" are used interchangeably and are intended to include any functional activity normally attributed to a selected polypeptide when produced under favorable conditions. The activity of a polysaccharase would be, for example, the ability of the polypeptide to enzymatically depolymerize a complex saccharide. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "secreted" is intended to include an increase in the secretion of a polypeptide, e.g., a heterologous polypeptide, preferably a polysaccharase. Typically, the polypeptide is secreted at an increased level that is in excess of the naturally-occurring amount of secretion. More preferably, the term "secreted" refers to an increase in secretion of a given polypeptide that is at least 10% and more preferably, at least 100%, 200%, 300,%, 400%, 500%, 600%, 700%, 800%, 900%, 1000%, or more, as compared to the naturally-occurring level of secretion.

The term "secretory polypeptide" is intended to include any polypeptide/s, alone or in combination with other polypeptides, that facilitate the transport of another polypeptide from the intracellular space of a cell to the extracellular milieu. In one embodiment, the secretory polypeptide/s encompass all the necessary secretory polypeptides sufficient to impart secretory activity to a Gram-negative host cell. Typically, secretory proteins are encoded in a single region or locus that may be isolated from one host cell and transferred to another host cell using genetic engineering. In a preferred embodiment, the secretory polypeptide/s are derived from any bacterial cell having secretory activity. In a more preferred embodiment, the secretory polypeptide/s are derived from a host cell having Type II secretory activity. In another more preferred embodiment, the host cell is selected from the family Enterobacteriaceae. In a most preferred embodiment, the secretory polypeptide/s are one or more gene products of the out or pul genes derived from, respectively, *Erwinia* or *Klebsiella*. Moreover, the skilled artisan will appreciate that any secretory protein/s derived from a related host that is sufficiently homologous to the out or pul gene/s described herein may also be employed (Pugsley et al., (1993) *Microbiological Reviews* 57:50–108; Lindeberg et al., (1996) *Mol. Micro.* 20:175–190; Lindeberg et al., (1992) *J. of Bacteriology* 174:7385–7397; He et al., (1991) *Proc. Natl. Acad. Sci. USA*, 88:1079–1083).

The term "derived from" is intended to include the isolation (in whole or in part) of a polynucleotide segment from an indicated source. The term is intended to include, for example, direct cloning, PCR amplification, or artificial synthesis from, or based on, a sequence associated with the indicated polynucleotide source.

The term "ethanologenic" is intended to include the ability of a microorganism to produce ethanol from a carbohydrate as a primary fermentation product. The term is intended to include naturally occurring ethanologenic organisms, ethanologenic organisms with naturally occurring or induced mutations, and ethanologenic organisms which have been genetically modified.

The term "Gram-negative bacteria" is intended to include the art recognized definition of this term. Typically, Gram-negative bacteria include, for example, the family Enterobacteriaceae which comprises, among others, the species *Escherichia* and *Klebsiella*.

The term "sufficiently homologous" is intended to include a first amino acid or nucleotide sequence which contains a sufficient or minimum number of identical or equivalent amino acid residues or nucleotides, e.g., an amino acid residue which has a similar side chain, to a second amino acid or nucleotide sequence such that the first and second amino acid or nucleotide sequences share common structural domains and/or a common functional activity. For example, amino acid or nucleotide sequences which share common structural domains have at least about 40% homology, preferably 50% homology, more preferably 60%, 70%, 80%, or 90% homology across the amino acid sequences of the domains and contain at least one, preferably two, more preferably three, and even more preferably four, five, or six structural domains, are defined herein as sufficiently homologous. Furthermore, amino acid or nucleotide sequences which share at least 40%, preferably 50%, more preferably 60%, 70%, 80%, or 90% homology and share a common functional activity are defined herein as sufficiently homologous.

In one embodiment, two polynucleotide segments, e.g., promoters, are "sufficiently homologous" if they have substantially the same regulatory effect as a result of a substantial identity in nucleotide sequence. Typically, "sufficiently homologous" sequences are at least 50%, more preferably at least 60%, 70%, 80%, or 90% identical, at least in regions known to be involved in the desired regulation. More preferably, no more than five bases differ. Most preferably, no more than five consecutive bases differ.

To determine the percent identity of two polynucleotide segments, or two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mod. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The polynucleotide and amino acid sequences of the present invention can further be used as a "query sequence" to perform a search against public databases to, for example, identify other family members or related sequences, e.g., promoter sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to polynucleotide molecules of the invention. BLAST protein searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

II. Recombinant Hosts

The present invention relates to recombinant host cells that are suitable for use in the production of ethanol. In one embodiment, the cell comprises a heterologous, polynucleotide segment encoding a polypeptide under the transcriptional control of a surrogate promoter. The heterologous polynucleotide and surrogate promoter may be plasmid-based or integrated into the genome of the organism (as described in the examples). In a preferred embodiment, the host cell is used as a source of a desired polypeptide for use in the bioconversion of a complex sugar to ethanol, or a step thereof.

In a preferred embodiment, the heterologous polynucleotide segment encodes a polysaccharase polypeptide which is expressed at higher levels than are naturally occurring in the host. The polysaccharase may be a β-glucosidase, a glucanase, either an endoglucanase or a exoglucanase, cellobiohydrolase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

In one embodiment, the polysaccharase is derived from *E. chrysanthemi* and is the glucanase (EGZ) polypeptide encoded by the celZ gene. However, other polysaccharases from *E. chrysanthemi* may be used including, e.g., the glucohydrolases encoded by celY (Guiseppi et al., (1991) *Gene* 106:109–114) or bgxA (Vroeman et al., (1995) *Mol. Gen. Genet.* 246:465–477). The celY gene product (EGY) is an endoglucanase. The bgxA gene encodes β-glucosidase and β-xylosidase activities (Vroeman et al., (1995) *Mol. Gen. Genet.* 246:465–477). Preferably, an increase in polysaccharase activity of at least 10%, more preferably 20%, 30%, 40%, or 50% is observed. Most preferably, an increase in polysaccharase activity of several fold is obtained, e.g., 200%, 300%, 400%, 500%, 600%, 700%, or 800%.

Alternatively, a desired polysaccharase may be encoded by a polynucleotide segment from another species, e.g., a yeast, an insect, an animal, or a plant. Any one or more of these genes may be introduced and expressed in the host cell of the invention in order to give rise to elevated levels of a polysaccharase suitable for depolymerizing a complex sugar substrate. The techniques for introducing and expressing one of these genes in a recombinant host, are presented in the examples.

In another embodiment of the invention, the host cell has been engineered to express a secretory protein/s to facilitate the export of a desired polypeptide from the cell. In one embodiment, the secretory protein or proteins are derived from a Gram-negative bacterial cell, e.g., a cell from the family Enterobacteriaceae. In another embodiment, the secretory protein/s are from *Erwinia* and are encoded by the out genes. In another embodiment, the secretory proteins are the pul genes derived from *Klebsiella*. The introduction of one or more of these secretory proteins is especially desirable if the host cell is an enteric bacterium, e.g., a Gram-negative bacterium having a cell wall. Representative Gram-negative host cells of the invention are from the family Enterobacteriaceae and include, e.g., *Escherichia* and *Klebsiella*. In one embodiment, the introduction of one or more secretory proteins into the host results in an increase in the secretion of the selected protein, e.g., a polysaccharase, as compared to naturally-occurring levels of secretion. Preferably, the increase in secretion is at least 10% and more preferably, 100%, 200%, 300%, 400%, 500%, 600%, 700%, 800%, 900%, 1000%, or more, as compared to naturally-occurring levels of secretion. In a preferred embodiment, the addition of secretion genes allows for the polysaccharase polypeptide to be produced at higher levels. In a preferred embodiment, the addition of secretion genes allows for the polysaccharase polypeptide to be produced with higher enzymatic activity. In a most preferred embodiment, the polysaccharase is produced at higher levels and with higher enzymatic activity. Preferably, an increase in polysaccharase activity of at least 10%, more preferably 20%, 30%, 40%, 50%, 60%, 70%, 80%, 90%, or 100% is observed. Most preferably, an increase in polysaccharase activity of several fold is obtained, e.g., 200%, 300%, 400%, 500%, 600%, 700%, 800%, 900%, or 1000%, as compared to cells without secretion genes (e.g., cells that either lack or do not express secretion genes at a sufficient level). The techniques and methods for introducing such genes and measuring increased output of a desired polypeptide such as, e.g., a polysaccharase, are described in further detail in the examples. Other equivalent methods are known to those skilled in the art.

In preferred embodiments, the invention makes use of a recombinant host that is also ethanologenic. In one embodiment, the recombinant host is a Gram-negative bacterium. In another embodiment, the recombinant host is from the family Enterobacteriaceae. The ethanologenic hosts of U.S. Pat. No. 5,821,093, hereby incorporated by reference, for example, are suitable hosts and include, in particular, *E. coli* strains KO4 (ATCC 55123), KO11 (ATCC 55124), and KO12 (ATCC 55125), and *Klebsiella oxytoca* strain M5A1. Alternatively, a non-ethanologenic host of the present invention may be convened into an ethanologenic host (such as the above-mentioned strains) by introducing, for example, ethanologenic genes from an efficient ethanol producer like *Zymomonas mobilis*. This type of genetic engineering, using standard techniques, results in a recombinant host capable of efficiently fermenting sugar into ethanol. In addition, the LY01 ethanol tolerant strain (ATCC PTA-3466) may be employed as described in published PCT international application WO 98/45425 and this published application is hereby incorporated by reference (see also, e.g., Yomano et al. (1993) *J. of Ind. Micro. & Bio.* 20:132–138).

In another preferred embodiment, the invention makes use of a non-ethanologenic recombinant host, e.g., *E. coli* strain B, *E. coli* strain DH5α, or *Klebsiella oxytoca* strain M5A1. These strains may be used to express a desired polypeptide, e.g., a polysaccharase using techniques describe herein. In addition, these recombinant host may be used in conjunction with another recombinant host that expresses, yet another desirable polypeptide, e.g., a different polysaccharase. In addition, the non-ethanologenic host cell may be used in conjunction with an ethanologenic host cell. For example, the use of a non-ethanologenic host/s for carrying out, e.g., the depolymerization of a complex sugar may be followed by the use of an ethanologenic host for fermenting the depolymerized sugar. Accordingly, it will be appreciated that these reactions may be carried out serially or contemporaneously using, e.g., homogeneous or mixed cultures of non-ethanologenic and ethanologenic recombinant hosts.

In a preferred embodiment, one or more genes necessary for fermenting a sugar substrate into ethanol are provided on a plasmid or integrated into the host chromosome. More preferably, essential genes for fermenting a sugar substrate into ethanol, e.g., pyruvate decarboxylase (e.g., pdc) and/or alcohol dehydrogenase (e.g., adh) are introduced into the host of the invention using an artificial operon such as the PET operon as described in U.S. Pat. No. 5,821,093, hereby incorporated by reference. Indeed, it will be appreciated that the present invention, in combination with what is known in the art, provides techniques and vectors for introducing multiple genes into a suitable host (see, e.g., *Current Protocols in Molecular Biology*, eds. Ausubel et al., John Wiley & Sons (1992), Sambrook, J. et al., *Molecular Cloning: A Laboratory Manual*. 2nd, ed, Cold Spring Harbor Laboratory, Cold Spring Harbor Laboratory Press, Cold Spring Harbor, N.Y. (1989), and *Bergey's Manual of Determinative Bacteriology*, Kreig et al., Williams and Wilkins (1984), hereby incorporated by reference). Accordingly, using the methods of the invention, a single genetic construct could encode all of the necessary gene products (e.g., a glucanase, an endoglucanase, an exoglucanase, a secretory protein/s, pyruvate decarboxylase, alcohol dehydrogenase) for performing simultaneous saccharification and fermentation (SSF). In addition, it will also be appreciated that such a host may be further manipulated, using methods known in the art, to have mutations in any endogenous gene/s (e.g., recombinase genes) that would interfere with the stability, expression, and function of the introduced genes. Further, it will also be appreciated that the invention is intended to encompass any regulatory elements, gene/s, or gene products, i.e., polypeptides, that are sufficiently homologous to the ones described herein.

Methods for screening strains having the introduced genes are routine and may be facilitated by visual screens that can identify cells expressing either the alcohol dehydrogenase (ADH) or glucanase (EGZ) gene product. The ADH gene product produces acetaldehyde that reacts with the leucosulfonic acid derivative of p-roseaniline to produce an intensely red product. Thus, ADH-positive clones can be easily screened and identified as bleeding red colonies. Methods for screening for EGZ, e.g., polysaccharase activity, also results in a clear visual phenotype as described below and in the examples.

Recombinant bacteria expressing, for example, the PET operon typically grow to higher cell densities in liquid culture than the unmodified parent organisms due to the production of neutral rather than acidic fermentation products (Ingram et al., (1988) *Appl. Environ. Microbiol.* 54:397–404). On plates, ethanologenic clones are readily apparent as large, raised colonies which appear much like yeast. These traits have been very useful during the construction of new strains and can provide a preliminary indication of the utility of new constructs. Rapid evaluations of ethanol producing potential can also be made by testing the speed of red spot development on aldehyde indicator plates (Conway et al., (1987) *J. Bacteriol.* 169:2591–2597). Typically, strains which prove to be efficient in sugar conversion to ethanol can be recognized by the production of red spots on aldehyde indicator plates within minutes of transfer.

In a most preferred embodiment of the invention, a single host cell is ethanologenic, that is, has all the necessary genes, either naturally occurring or artificially introduced or enhanced (e.g., using a surrogate promoter and/or genes from a different species or strain), such that the host cell has the ability to produce and secrete a polysaccharase/s, degrade a complex sugar, and ferment the degraded sugar into ethanol. Accordingly, such a host is suitable for simultaneous saccharification and fermentation.

Moreover, the present invention takes into account that the native *E. coli* fermentation pathways produce a mixture of acidic and neutral products (in order of abundance): lactic acid, hydrogen+carbon dioxide (from formate), acetic acid, ethanol, and succinate. However, the *Z. mobilis* PDC (pyruvate decarboxylase) has a lower Km for pyruvate than any of the competing *E. coli* enzymes. By expressing high activities of PDC, carbon flow is effectively redirected from lactic acid and acetyl-CoA into acetylaldehyde and ethanol. Small amounts of phosphoenolpyruvate can be eliminated by deleting the fumarate reductase gene (frd) (Ingram et al., (1991) U.S. Pat. No. 5,000,000; Ohta et al., (1991) *Appl. Environ. Microbiol.* 57:893–900). Additional mutations (e.g., in the pfl or ldh genes) may be made to completely eliminate other competing pathways (Ingram et al., (1991) U.S. Pat. No. 5,000,000). Additional mutations to remove enzymes (e.g., recombinases, such as recA) that may compromise the stability of the introduced genes (either plasmid-based or integrated into the genome) may also be introduced, selected for, or chosen from a particular background.

In addition, it should be readily apparent to one skilled in the art that the ability conferred by the present invention, to transform genes coding for a protein or an entire metabolic pathway into a single manipulable construct, is extremely useful. Envisioned in this regard, for example, is the application of the present invention to a variety of situations where genes from different genetic loci are placed on a chromosome. This may be a multi-cistronic cassette under the control of a single promoter or separate promoters may be used.

Exemplary *E. coli* strains that are ethanologenic and suitable for further improvement according to the methods of the invention include, for example, KO4, KO11, and KO12 strains, as well as the LY01 strain, an ethanol-tolerant mutant of the *E. coli* strain KO11. Ideally, these strains may be derived from the *E. coli* strain ATCC 11303, which is hardy to environmental stresses and can be engineered to be ethanologenic and secrete a polysaccharase/s. In addition, recent PCR investigations have confirmed that the ATCC 11303 strain lacks all genes known to be associated with the pathogenicity of *E. coli* (Kuhnert et al., (1997) *Appl. Environ. Microbiol.* 63:703–709).

Another preferred ethanologenic host for improvement according to the methods of the invention is the *E. coli* KO11 strain which is capable of fermenting hemicellulose hydrolysates from many different lignocellulosic materials and other substrates (Asghari et al., (1996) *J. Ind. Microbiol.* 16:42–47; Barbosa et al., (1992) *Current Microbiol.* 28:279–282; Beall et al., (1991) *Biotechnol. Bioeng.* 38:296–303; Beall et al., (1992) *Biotechnol. Lett.* 14:857–862; Hahn-Hagerdal et al., (1994) *Appl. Microbiol. Biotechnol.* 41:62–72; Moniruzzaman et al., (1996) *Biotechnol. Lett.* 18:955–990; Moniruzzaman et al., (1998) *Biotechnol. Lett.* 20:943–947; Grohmann et al., (1994) *Biotechnol. Lett.* 16:281–286; Guimaraes et al., (1992) *Biotechnol. Bioeng.* 40:41–45; Guimaraes et al., (1992) *Biotechnol. Lett.* 14:415–420; Moniruzzaman et al., (1997) *J. Bacteriol.* 179: 1880–1886). In FIG. 1, the kinetics of bioconversion for this strain are shown. In particular, this strain is able to rapidly ferment a hemicellulose hydrolysate from rice hulls (which contained 58.5 g/L of pentose sugars and 37 g/L of hexose sugars) into ethanol (Moniruzzaman et al., (1998) *Biotechnol. Lett.* 20:943–947). It was noted that this strain was capable of fermenting a hemicellulose hydrolysate to completion within 48 to 72 hours, and under ideal conditions, within 24 hours.

Another preferred host cell of the invention is the bacterium *Klebsiella*. In particular, *Klebsiella oxytoca* is preferred because, like *E. coli*, this enteric bacterium has the native ability to metabolize monomeric sugars, which are the constituents of more complex sugars. Moreover, *K. oxytoca* has the added advantage of being able to transport and metabolize cellobiose and cellotriose, the soluble intermediates from the enzymatic hydrolysis of cellulose (Lai et al., (1996) *Appl. Environ. Microbiol.* 63:355–363; Moniruzzaman et al., (1997) *Appl. Environ. Microbiol.* 63:4633–4637; Wood et al., (1992) *Appl. Environ. Microbiol.* 58:2103–2110). The invention provides genetically engineered ethanologenic derivatives of *K. oxytoca*, e.g., strain M5A1 having the *Z. mobilis* pdc and adhB genes encoded within the PET operon (as described herein and in U.S. Pat. No. 5,821,093; Wood et al., (1992) *Appl. Environ. Microbiol.* 58:2103–2110).

Accordingly, the resulting organism, strain P2, produces ethanol efficiently from monomer sugars and from a variety of saccharides including raffinose, stachyose, sucrose, cellobiose, cellotriose, xylobiose, xylotriose, maltose, etc. (Burchhardt et al., (1992) *Appl. Environ. Microbiol.* 58:1128–1133; Moniruzzaman et al., (1997) *Appl. Environ. Microbiol* 63:4633–4637; Moniruzzaman et al., (1997) *J. Bacteriol.* 179:1880–1886; Wood et al., (1992) *Appl. Environ. Microbiol.* 58:2103–2110). These strains may be further modified according to the methods of the invention to express and secrete a polysaccharase. Accordingly, this strain is suitable for use in the bioconversion of a complex saccharide in an SSF process (Doran et al., (1993) *Biotechnol. Progress.* 9:533–538; Doran et al., (1994) *Biotechnol. Bioeng.* 44:240–247; Wood et al., (1992) *Appl. Environ. Microbiol.* 58:2103–2110). In particular, the use of this ethanologenic P2 strain eliminates the need to add supplemental cellobiase, and this is one of the least stable components of commercial fungal cellulases (Grohmann, (1994) *Biotechnol. Lett.* 16:281–286).

Screen for Promoters Suitable for use in Heterologous Gene Expression

While in one embodiment, the surrogate promoter of the invention is used to improve the expression of a heterologous gene, e.g., a polysaccharase, it will be appreciated that the invention also allows for the screening of surrogate promoters suitable for enhancing the expression of any desirable gene product. In general, the screening method makes use of the cloning vector described in Example 1 and depicted in FIG. 3 that allows for candidate promoter fragments to be conveniently ligated and operably-linked to a reporter gene. In one embodiment, the celZ gene encoding glucanase serves as a convenient reporter gene because a strong calorimetric change results from the expression of this enzyme (glucanase) when cells bearing the plasmid are grown on a particular media (CMC plates). Accordingly, candidate promoters, e.g., a particular promoter sequence or, alternatively, random sequences that can be "shotgun" cloned and operably linked to the vector, can be introduced into a host cell and resultant colonies are scanned, visually, for having increased gene expression as evidenced by a phenotypic glucanase-mediated colorimetric change on a CMC plate. Colonies having the desired phenotype are then processed to yield the transforming DNA and the promoter is sequenced using appropriate primers (see Example 1 for more details).

Figure 4:
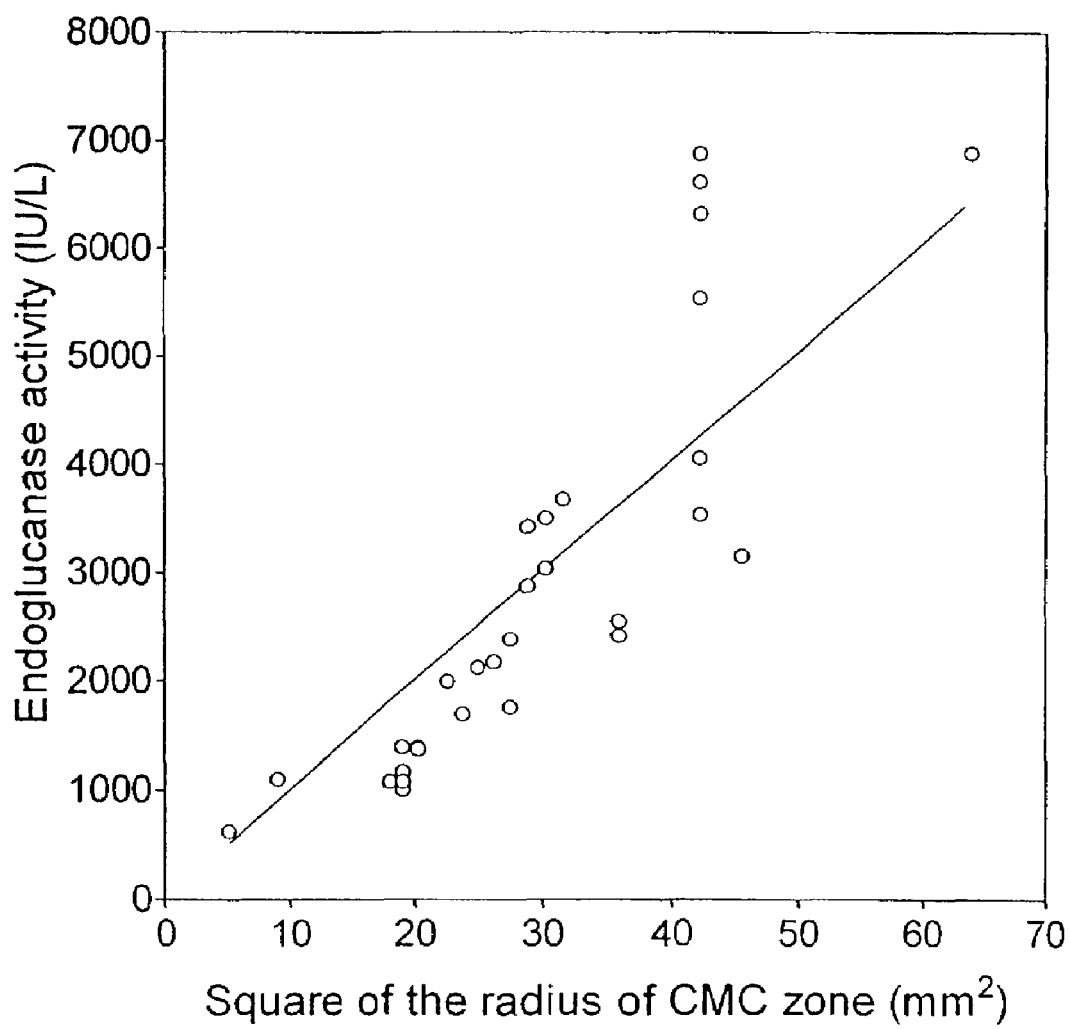
FIG. 4 is a graph showing the high correspondence between the size of the zone of clearance on CMC indicator plates (x-axis) measured for a transformed bacterial colony and the amount of glucanase activity expressed (y-axis).

The high correspondence between the glucanase-mediated colorimetric change on a CMC plate and expression levels of the enzyme is an excellent indication of the strength of a candidate promoter (FIG. 4). Hence, the methods of invention provide a rapid visual test for rating the strength of candidate surrogate promoters. Accordingly, depending on the desired expression level needed for a specific gene product, a particular identified surrogate promoter can be selected using this assay. For example, if simply the highest expression level is desired, then the candidate promoter that produces the largest colorimetric change may be selected. If a lower level of expression is desired, for example, because the intended product to be expressed is toxic at high levels or must be expressed at equivalent levels with another product, a weaker surrogate promoter can be identified, selected, and used as described.

III. Methods of use

Degrading or Depolymerizing a Complex Saccharide

In one embodiment, the host cell of the invention is used to degrade or depolymerize a complex sugar e.g., lignocellulose or an oligosaccharide into a smaller sugar moiety. To accomplish this, the host cell of the invention preferably expresses one or more polysaccharases, e.g., a glucanase, and these polysaccharases may be liberated naturally from the producer organism. Alternatively, the polysaccharase is liberated from the producer cell by physically disrupting the cell. Various methods for mechanically (e.g., shearing, sonication), enzymatically (e.g., lysozyme), or chemically disrupting cells, are known in the art, and any of these methods may be employed. Once the desired polypeptide is liberated from the inner cell space it may be used to degrade a complex saccharide substrate into smaller sugar moieties for subsequent bioconversion into ethanol. The liberated cellulase may be purified using standard biochemical techniques known in the art. Alternatively, the liberated polysaccharide need not be purified or isolated from the other cellular components and can be applied directly to the sugar substrate.

In another embodiment, a host cell is employed that coexpresses a polysaccharase and a secretory protein/s such that the polysaccharase is secreted into the growth medium. This eliminates the above-mentioned step of having to liberate the polysaccharase from the host cell. When employing this type of host, the host may be used directly in an aqueous solution containing a complex saccharide.

In another embodiment, a host cell of the invention is designed to express more than one polysaccharase or is mixed with another host expressing a different polysaccharase. For example, one host cell could express a heterologous β-glucosidase while another host cell could express an endoglucanase and yet another host cell could express an exoglucanase, and these cells could be combined to form a heterogeneous culture having multiple polysaccharase activities. Alternatively, in a preferred embodiment, a single host strain is engineered to produce all of the above polysaccharases. In either case, a culture of recombinant host/s is produced having high expression of the desired polysaccharases for application to a sugar substrate. If desired, this mixture can be combined with an additional cellulase, e.g., an exogenous cellulase, such as a fungal cellulase. This mixture is then used to degrade a complex substrate. Alternatively, prior to the addition of the complex sugar substrate, the polysaccharase/s are purified from the cells and/or media using standard biochemical techniques and used as a pure enzyme source for depolymerizing a sugar substrate.

Finally, it will be appreciated by the skilled artisan, that the ethanol-producing bacterial strains of the invention are superior hosts for the production of recombinant proteins because, under anaerobic conditions (e.g., in the absence of oxygen), there is less opportunity for improper folding of the protein (e.g., due to inappropriate disulfide bond formation). Thus, the hosts and culture conditions of the invention potentially result in the greater recovery of a biologically active product.

Fermenting a Complex Saccharide

In a preferred embodiment of the present invention, the host cell having the above mentioned attributes is also ethanologenic. Accordingly, such a host cell can be applied in degrading or depolymerizing a complex saccharide into a monosaccharide. Subsequently, the cell can catabolize the simpler sugar into ethanol by fermentation. This process of concurrent complex saccharide depolymerization into smaller sugar residues followed by fermentation is referred to as simultaneous saccharification and fermentation.

Typically, fermentation conditions are selected that provide an optimal pH and temperature for promoting the best growth kinetics of the producer host cell strain and catalytic conditions for the enzymes produced by the culture (Doran et al., (1993) *Biotechnol. Progress.* 9:533–538). For example, for *Klebsiella,* e.g., the P2 strain, optimal conditions were determined to be between 35–37° C. and pH 5.0–pH 5.4. Under these conditions, even exogenously added fungal endoglucanases and exoglucanases are quite stable and continue to function for long periods of time. Other conditions are discussed in the Examples. Moreover, it will be appreciated by the skilled artisan, that only routine experimentation is needed, using techniques known in the art, for optimizing a given fermentation reaction of the invention.

Currently, the conversion of a complex saccharide such as lignocellulose, is a very involved, multi-step process. For example, the lignocellulose must first be degraded or depolymerized using acid hydrolysis. This is then followed by steps that separate liquids from solids and these products are subsequently washed and detoxified to result in cellulose and hemicellulose that can be further depolymerized (using added cellulases) and finally, fermented by a suitable ethanologenic host cell. In contrast, the fermenting of corn is much simpler in that amylases can be used to break down the corn starch for immediate bioconversion by an ethanologenic host in essentially a one-step process. Accordingly, it will be appreciated by the skilled artisan that the recombinant hosts and methods of the invention afford the use of a similarly simpler and more efficient process for fermenting lignocellulose. For example, the method of the invention is intended to encompass a method that avoids acid hydrolysis altogether. Moreover, the hosts of the invention have the following advantages, 1) efficiency of pentose and hexose co-fermentation; 2) resistance to toxins; 3) production of enzymes for complex saccharide depolymerization; and 4) environmental hardiness. Accordingly, the complexity of depolymerizing lignocellulose can be simplified using an improved biocatalyst of the invention. Indeed, in one preferred embodiment of the invention, the reaction can be conducted in a single reaction vessel and in the absence of acid hydrolysis, e.g., as an SSF process.

Potential Substrates for Bioconversion into Ethanol

One advantage of the invention is the ability to use a saccharide source that has been, heretofore, underutilized.

A number of complex saccharide substrates may be used as a starting source for depolymerization and subsequent fermentation using the host cells and methods of the invention. Ideally, a recyclable resource may be used in the SSF process. Mixed waste office paper is a preferred substrate (Brooks et al., (1995) *Biotechnol. Progress.* 11:619–625; Ingram et al., (1995) U.S. Pat. No. 5,424,202), and is much more readily digested than acid pretreated bagasse (Doran et al., (1994) *Biotech. Bioeng.* 44:240–247) or highly purified crystalline cellulose (Doran et al. (1993) *Biotechnol. Progress.* 9:533–538). Since glucanases, both endoglucanases and exoglucanases, contain a cellulose binding domain, and these enzymes can be readily recycled for subsequent fermentations by harvesting the undigested cellulose residue using centrifugation (Brooks et al., (1995) *Biotechnol. Progress.* 11:619–625). By adding this residue with bound enzyme as a starter, ethanol yields (per unit substrate) were increased to over 80% of the theoretical yield with a concurrent 60% reduction in fungal enzyme usage (FIG. 2). Such approaches work well with purified cellulose, although the number of recycling steps may be limited with substrates with a higher lignin content. Other substrate sources that are within the scope of the invention include any type of processed or unprocessed plant material, e.g., lawn clippings, husks, cobs, stems, leaves, fibers, pulp, hemp, sawdust, newspapers, etc.

This invention is further illustrated by the following examples which should not be construed as limiting.

EXAMPLE 1

**Methods for Making Recombinant *Escherichia* Hosts Suitable for Fermenting Oligosaccharides into Ethanol**

In this example, methods for developing and using *Escherichia* hosts suitable for fermenting oligosaccharides into ethanol are described. In particular, a strong promoter is identified which can be used to increase the expression of a polysaccharase (e.g., glucanase). In addition, genes from *Erwinia chrysanthemi* are employed to facilitate polysaccharase secretion thereby eliminating the need for cell disruption in order to release the desired polysaccharase activity.

Throughout this example, the following materials and methods are used unless otherwise stated.

Materials and Methods

Organisms and Culture Conditions

The bacterial strains and plasmids used in this example are listed in Table 1, below.

For plasmid constructions, the host cell *E. coli* DH5α was used. The particular gene employed encoding a polysaccharase (e.g., glucanase) was the celZ gene derived from *Erwinia chrysanthemi* P86021 (Beall, (1995) Ph.D. Dissertation, University of Florida; Wood et al., (1997) *Biotech. Bioeng.* 55:547–555). The particular genes used for improving secretion were the out genes derived from *E. chrysanthemi* EC 16 (He et al., (1991) *Proc. Natl. Acad. Sci. USA.* 88:1079–1083).

Typically, host cell cultures were grown in Luria-Bertani broth (LB) (10 g $L^{-1}$ Difco® tryptone, 5 g $L^{-1}$ Difco® yeast extract, 5 g $L^{-1}$ sodium chloride) or on Luria agar (LB supplemented with 15 g $L^{-1}$ of agar). For screening host cells having glucanase celZ activity (EGZ), CMC-plates (Luria agar plates containing carboxymethyl cellulose (3 g $L^{-1}$)) were used (Wood et al., (1988) *Methods in Enzymology* 160:87–112). When appropriate, the antibiotics ampicillin (50 mg $L^{-1}$), spectinomycin (100 g $L^{-1}$), kanamycin (50 g $L^{-1}$) were added to the media for selection of recombinant or integrant host cells containing resistance markers. Constructs containing plasmids with a temperature conditional pSC101 replicon (Posfai et al., (1997) *J. Bacteriol.* 179:4426–4428) were grown at 30° C. and, unless stated otherwise, constructs with pUC-based plasmids were grown at 37° C.

TABLE 1

Strains and Plasmids Used

| Strains/Plasmids | Description | Sources/References |
|---|---|---|
| Strains | | |
| *Z. mobilis* CP4 | Prototrophic | Osman et al., (1985) J. Bact. 164:173–180 |
| *E. coli* strain DH5α | lacZ M15 recA | Bethesda Research Laboratory |
| *E. coli* strain B | prototrophic | ATCC 11303 |
| *E. coli* strain HB 101 | recA lacY recA | ATCC 37159 |
| Plasmids | | |
| pUC19 | bla cloning vector | New England Biolabs |
| pST76-K | kan low copy number, temp. sens. | |
| pRK2013 | kan mobilizing helper plasmid (mob+) | ATCC |
| pCPP2006 | SP$^r$, ca. 40 kbp plasmid carrying the complete out genes from *E. chrysanthemi* EC16 | He et al., (1991) P.N.A.S. 88:1079–1083 |
| pLOI1620 | b/a celZ | Beall et al, (1995) Ph.D. Dissertation, U. of Florida |
| pLOI2164 | pLOI1620 with BamHI site removed (Klenow) | See text |
| pLOI2170 | NdeI-HindIII fragment (promoterless celZ) from pLOI2164 cloned into pUC19 | See text |
| pLOI2171 | BamHI-SphI fragment (promoterless celZ) from pLOI2170 cloned into pST76-K | See text |
| pLOI2173 | EcoRI-SphI fragment (celZ with native promoter) from pLOI2164 cloned into pST76-K | See text |
| pLOI2174 | EcoRI-BamHI fragment (gap promoter) cloned into pLOI2171 | See text |
| pLOI2175 | EcoRI-BamHI fragment (eno promoter) cloned into pLOI2171 | See text |
| pLOI2177 | Random Sau3A1 *Z. mobilis* DNA fragment cloned into pLOI2171 | See text |
| pLOI2178 | Random Sau3A1 *Z. mobilis* DNA fragment cloned into pLOI2171 | See text |
| pLOI2179 | Random Sau3A1 *Z. mobilis* DNA fragment cloned into pLOI2171 | See text |
| pLOI2180 | Random Sau3A1 *Z. mobilis* DNA fragment cloned into pLOI2171 | See text |
| pLOI2181 | Random Sau3A1 *Z. mobilis* DNA fragment cloned into pLOI2171 | See text |
| pLOI2182 | Random Sau3A1 *Z. mobilis* DNA fragment cloned into pLOI2171 | See text |
| pLOI2183 | Random Sau3A1 *Z. mobilis* DNA fragment cloned into pLOI2171 | See text |
| pLOI2184 | Random Sau3A1 *Z. mobilis* DNA fragment cloned into pLOI2171 | See text |
| pLOI2196 | pLOI2177 fused into pUC19 at the PstI site | See text |

TABLE 1-continued

Strains and Plasmids Used

| Strains/Plasmids | Description | Sources/References |
|---|---|---|
| pLOI2197 | pLOI2180 fused into pUC19 at the PstI site | See text |
| pLOI2198 | pLOI2182 fused into pUC19 at the PstI site | See text |
| pLOI2199 | pLOI2183 fused into pUC19 at the PstI site | See text |
| pLOI2307 | EcoRI-SphI fragment from pLOI2183 cloned into pUC19 | See text |

Genetic Methods

Standard techniques were used for all plasmid constructions (Ausubel et al., (1987) *Current Protocols in Molecular Biology*, John Wiley & Sons, Inc.; Sambrook et al., (1989) *Molecular cloning: a laboratory manual*, $2^{nd}$ ed. C.S.H.L., Cold Spring Harbor, N.Y). For conducting small-scale plasmid isolation, the TELT procedure was performed. For large-scale plasmid isolation, the Promega® Wizard Kit was used. For isolating DNA fragments from gels, the Qiaquick® Gel Extraction Kit from Qiagen® was employed. To isolate chromosomal DNA from *E. coli* and *Z. mobilis* the methods of Cutting and Yomano were used (Cutting et al., (1990), Genetic analysis, pp. 61–74, In, Molecular biological methods for *Bacillus*, John Wiley & Sons, Inc.; Yomano et al., (1993) *J. Bacteriol.* 175:3926–3933).

To isolate the two glycolytic gene promoters (e.g., gap and eno) described herein, purified chromosomal DNA from *E. coli* DH5α was used as a template for the PCR (polymerase chain reaction) amplification of these nucleic acids using the following primer pairs: gap promoter, 5'-CGAAT-TCCTGCCGAAGTTTATTAGCCA-3' (SEQ ID NO: 3) and 5'-AAGGATCCTTCCACCAGCTATTTGTTAGTGA-3' (SEQ ID NO: 4); eno promoter, 5'-AGAATTCTGCCAGT-TGGTTGACGATAG-3' (SEQ ID NO: 5) and 5'-CAG-GATCCCCTCAAGTCACTAGTTAAACTG-3' (SEQ ID NO: 6). The out genes encoding secretory proteins derived from *E. chrysanthemi* (pCPP2006) were conjugated into *E. coli* using pRK2013 for mobilization (Figurski et al., (1979) *Proc. Natl. Acad. Sci. USA*. 76: 1648–1652; Murata et al., (1990) *J. Bacteriol.* 172:2970–2978).

To determine the sequence of various DNAs of interest, the dideoxy sequencing method using fluorescent primers was performed on a LI-COR Model 4000-L DNA Sequencer. The pST76-K-based plasmids were sequenced in one direction using a T7 primer (5'-TAATACGACTCAC-TATAGGG-3' (SEQ ID NO: 7)). The pUC18- and pUCI9-based plasmids were sequenced in two directions using either a forward primer (5'-CACGACGTTGTAAAAC-GAC-3' (SEQ ID NO: 8)) or a reverse primer (5'-TAA-CAATTTCACACAGGA-3' (SEQ ID NO: 9)). The extension reactions of the sequencing method were performed using a Perkin Elmer GeneAmp® PCR 9600 and SequiTherm Long-Read Sequencing Kit-LC®. Resultant sequences were subsequently analyzed using the Wisconsin Genetic Computer Group (GCG) software package (Devereux et al., (1984) *Nucleic Acids Rev.* 12:387–395).

To determine the start of transcriptional initiation in the above-mentioned promoters, primer extension analysis was performed using standard techniques. In particular, promoter regions were identified by mapping the transcriptional start sites using a primer finding correspondence within the celZ gene RNA that was isolated from cells in late exponential phase using a Qiagen RNeasy® kit. Briefly, cells were treated with lysozyme (400 µg/ml) in TE (Tris-HCl, EDTA) containing 0.2 M sucrose and incubated at 25° C. for 5 min prior to lysis. Liberated RNA was subjected to ethanol precipitation and subsequently dissolved in 20 µl of Promega® AMV reverse transcriptase buffer (50 mM Tris-HCl, pH 8.3, 50 mM KCl, 10 mM $MgCl_2$, 0.5 mM spermadine, 10 mM DTT). An IRD41-labeled primer (5'-GACTGGATGGTTATCCGAATAAGAGAGAGG-3' (SEQ ID NO: 10)) from LI-Cor Inc. was then added and the sample was denatured at 80° C. for 5 min, annealed at 55° C. for 1 hr, and purified by alcohol precipitation. Annealed samples were dissolved in 19 µl of AMV reverse transcriptase buffer containing 500 µM dNTPs and 10 units AMV reverse transcriptase, and incubated for extension (1 h at 42° C.). Products were treated with 0.5 µg/ml DNase-free RNase A, precipitated, dissolved in loading buffer, and compared to parallel dideoxy promoter sequences obtained using the LI-COR Model 4000-L DNA sequencer.

Polysaccharase Activity

To determine the amount of polysaccharase activity (e.g., glucanase activity) resulting from expression of the celZ gene, a Congo Red procedure was used (Wood et al., (1988) *Methods in Enzymology* 160:87–112). In particular, selected clones were transferred to gridded CMC plates and incubated for 18 h at 30° C. and then stained and recombinant host cells expressing glucanase formed yellow zones on a red background. Accordingly, the diameters of these colorimetric zones were recorded as a relative measure of celZ expression.

Glucanase activity (EGZ) was also measured using carboxymethyl cellulose as a substrate. In this test, appropriate dilutions of cell-free culture broth (extracellular activity) or broth containing cells treated with ultrasound (total activity) were assayed at 35° C. in 50 mM citrate buffer (pH 5.2) containing carboxymethyl cellulose (20 g $L^{-1}$). Conditions for optimal enzyme release for 3–4 ml samples were determined to be 4 pulses at full power for 1 second each using a cell disruptor (Model W-220F, Heat System-Ultrasonics Inc., Plainview, N.Y.). To stop the enzyme reactions of the assay, samples were heated in a boiling water bath for 10 min. To measure reducing sugars liberated enzymatically by the glucanase, a dinitrosalicylic acid reagent was employed using glucose as a standard (Wood et al., (1988) *Methods in Enzymology* 160:87–112). The amount of enzyme activity (IU) was expressed as µmols of reducing sugar released per min or as a percentage of total activity from an average of two or more determinations.

Ultrastructural Analysis

To determine the ultrastructure of various recombinant host cells, fresh colonies from Luria agar plates were prepared for analysis by fixing in 2% glutaraldehyde in 0.2 M sodium cacodylate buffer (pH 7) followed by incubation in 1% osmium tetroxide and followed by 1% uranyl acetate in distilled water. Samples were dehydrated in ethanol, embedded in Spurr's plastic, and ultrathin sections were prepared and examined using a Zeiss® EM-IOCA electron microscope (Spur (1969) *J. Ultrastruct. Res.* 26:31).

Figure 3:
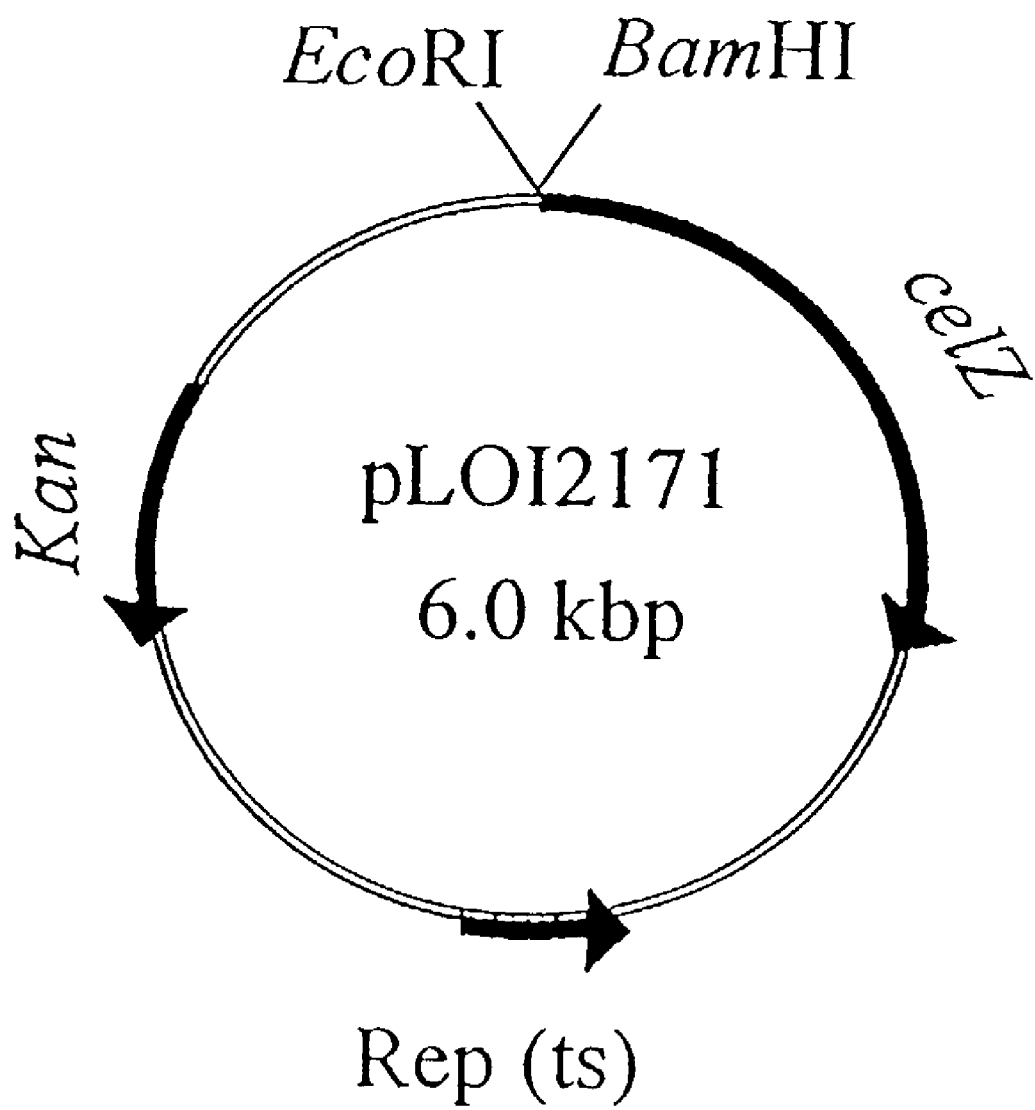
FIG. 3 shows the structure of the plasmid pLOI2171, a low copy promoter probe vector showing the orientation of the kanamycin resistance gene (kan) for selection, the temperature sensitive pSC101 replicon (Rep(ts)) for episomal maintenance of the plasmid, and the promoterless polysaccharase gene celZ encoding glucanase (EGZ).

Construction of a Low Copy Promoter Probe Vector Using celZ as the Reporter Gene To facilitate the isolation of strong promoters, a low copy vector was constructed with a pSC101 replicon and a BamHI site immediately preceding a promoterless celZ gene (pLOI2171). Accordingly, this promoterless plasmid was used as a negative control. The plasmid pLOI1620 was used as a source of celZ and is a pUC18 derivative with expression from consecutive lac and celZ promoters. The BamHI site in this plasmid was eliminated by digestion and Klenow treatment (pLOI2164). The celZ gene was isolated as a promoterless NdeI fragment after Klenow treatment. The resulting blunt fragment was digested with HindIII to remove downstream DNA and ligated into pUC19 (HindIII to HincII) to produce pLOI2170. In this plasmid, celZ is oriented opposite to the direction of lacZ transcription and was only weakly expressed. The BamHI (amino terminus)-SphI (carboxyl terminus) fragment from pLOI2170 containing celZ was then cloned into the corresponding sites of pST76-K, a low copy vector with a temperature sensitive replicon, to produce pLOI2171 (FIG. 3). Expression of celZ in this vector was extremely low facilitating its use as a probe for candidate strong promoters.

Analysis of celZ Expression from Two E. coli Glycolytic Promoters (gap and eno)

Two exemplary promoters driving glycolytic genes (gap and eno) in E. coli were examined for their ability to drive the expression of the heterologous celZ gene encoding glucanase. Chromosomal DNA from the E. coli DH5α strain was used as a template to amplify the gap and eno promoter regions by the polymerase chain reaction. The resulting fragments of approximately 400 bp each were digested with EcoRI and BamHI and cloned into the corresponding sites in front of a promoterless celZ gene in pLOI2171 to produce pLOI2174 (gap promoter) and pLOI2175 (eno promoter). As a control, the EcoRI-SphI fragment from pLOI2164 containing the complete celZ gene and native E. chrysanthemi promoter was cloned into the corresponding sites of pST76-K to produce pLOI2173. These three plasmids were transformed into E. coli strains B and DH5α and glucanase activity (EGZ) was compared. For both strains of E. coli, glucanase activities were lower on CMC plates with E. coli glycolytic promoters than with pLOI2173 containing the native E. chrysanthemi promoter (Table 2). Assuming activity is related to the square of the radius of each zone (Fick's Law of diffusion), EGZ production with glycolytic promoters (pLOI2174 and pLOI2175) was estimated to be 33% to 65% lower than in the original construct. Accordingly, other candidate promoters for driving high levels of celZ gene expression were investigated.

Identifying and Cloning Random DNA Fragments Suitable for Use as Promoters for Heterologous Gene Expression Random fragments derived from Z. mobilis can be an effective source of surrogate promoters for the high level expression of heterologous genes in E. coli. (Conway et al., (1987) J. Bacteriol. 169:2327–2335; Ingram et al., (1988) Appl. Environ. Micro. 54:397–404). Accordingly, to identify surrogate promoters for Erwinia celZ expression, Z. mobilis chromosomal DNA was extensively digested with Sau3AI and resulting fragments were ligated into pLOI2171 at the BamHI site and transformed into E. coli DH5α to generate a library of potential candidate promoters. To rapidly identify superior candidate promoters capable of driving celZ gene expression in E. coli, the following biological screen was employed. Colonies transformed with celZ plasmids having different random candidate promoters were transferred to gridded CMC plates and stained for glucanase activity after incubation (Table 2). Approximately 20% of the 18,000 clones tested were CMC positive. The 75 clones which produced larger zones than the control, pLOI2173, were examined further using another strain, E. coli B.

TABLE 2

Evaluation of promoter strength for celZ expression in E. coli using CMC indicator plates.

| | E. coli DH5α host | | | E. coli B host | | |
|---|---|---|---|---|---|---|
| Plasmids | Number of Plasmids[a] | CMC zone diameter (mm)[b] | % of native promoter (100* $R^2_x/h^2_c$)[c] | Number of plasmids | CMC zone diameter (mm) | % of native promoter (100* $R^2_x/R^2_c$) |
| pLOI2171 (promoterless) | 1 | 0 | — | — | — | — |
| pLOI2173 (native promoter) | 1 | 5.0 | 100 | 1 | 4.5 | 100 |
| pLOI2174 (gap promoter) | 1 | 4.0 | 77 | 1 | 3.5 | 60 |
| pLOI2175 (eno promoter) | 1 | 3.0 | 43 | 1 | 2.8 | 35 |
| Z. mobilis promoters | | | | | | |
| Group I | 5 | 13.0 | 676 | 4 | 10.8–11.3 | 570–625 |
| Group II | 14 | 9.0–11.0 | 324–484 | 17 | 9.0–10.5 | 445–545 |
| Group III | 56 | 6.0–9.0 | 144–324 | 54 | 5.0–8.8 | 125–375 |

[a]The number of clones which the indicated range of activities.
[b]The average size of the diameters from three CMC digestion zones.
[c]$R^2_x$ is the square of the radius of the clear zone with the test plasmid; $R^2_c$ is the square of the radius of the clear zone for the control (pLOI2173).

Thus, promoter strength for selected candidate promoters was confirmed in two different strains with, in general, recombinants of DH5α producing larger zones (e.g., more glucanase) than recombinants of strain B. However, relative promoter strength in each host was similar for most clones. Based on these analyses of glucanase production as measured by zone size using CMC plates, four clones appeared to express celZ at approximately 6-fold higher levels than the construct with the original *E. chrysanthemi* celZ gene (pLOI2173), and at 10-fold higher levels than either of the *E. coli* glycolytic promoters. Accordingly, these and similarly strong candidate promoters were selected for further study.

Production and Secretion of Glucanase

Eight plasmid derivatives of pST76-K (pLOI2177 to pLOI2184) were selected from the above-described screen (see Group I and Group II (Table 2)) and assayed for total glucanase activity in *E. coli* strain B (Table 3). The four plasmids giving rise to the largest zones on CMC plates were also confirmed to have the highest glucanase activities (pLOI2177, pLOI2180, pLOI2182, and pLOI2183). The activities were approximately 6-fold higher than that of the unmodified celZ (pLOI2173), in excellent agreement with our estimate using the square of the radius of the cleared zone on CMC plates. FIG. 4 shows a comparison of activity estimates from CMC plates and in vitro enzyme assays for strain B containing a variety of different promoters, with and without the addition of out genes encoding secretory proteins. Although there is some scatter, a direct relationship is clearly evident which validates the plate method for estimating relative activity. The original construct in pUC18, a high copy plasmid, was also included for comparison (pLOI2164). This construct with consecutive lac and celZ promoters produced less EGZ activity than three of the low copy plasmids with surrogate promoters (pLOI2177, pLOI2182, and pLOI2183). Thus, to increase celZ expression of glucanase even more, the DNA fragment containing celZ and the most effective surrogate promoter was isolated from pLOI2183 (as a EcoRI-SphI fragment) and inserted into pUC19 with transcription oriented opposite to that of the lac promoter (pLOI2307). Accordingly, the above-identified strong surrogate promoter when incorporated into a high copy plasmid, further increased glucanase activity by 2-fold.

Engineering Increased Secretion of Glucanase

To further improve on the above-described results for increasing expression of celZ encoded glucanase, the above host cells were engineered for increased secretion. Genes encoding secretory proteins (e.g., the out genes) derived from *E. chrysanthemi* EC16 were used for improving the export of the glucanase using the plasmid as described in He et al. that contains out genes (pCPP2006) (He et al., (1991) *Proc. Natl. Acad. Sci. USA*. 88:1079–1083). The increased secretion of EGZ in *E. coli* B was investigated and results are presented in Table 3.

TABLE 3

Comparison of promoters for EGZ production and secretion in *E. coli* B

| Plasmids[a] | Without secretion genes | | With secretion genes (pCPP2006) | |
|---|---|---|---|---|
| | Total activity (IU/L)[b] | Extracellular[c] (%) | Total Activity (IU/L) | Extracellular[c] (%) |
| pLOI2173 | 620 | 17 | 1,100 | 43 |
| pLOI2177 | 3,700 | 10 | 5,500 | 44 |
| pLOI2178 | 2,200 | 9 | 3,500 | 49 |
| pLOI2179 | 2,000 | 10 | 3,000 | 50 |
| pLOI2180 | 2,900 | 8 | 6,300 | 39 |
| pLOI2181 | 1,800 | 11 | 4,100 | 46 |
| pLOI2182 | 3,500 | 7 | 6,600 | 38 |
| pLOI2183 | 3,400 | 7 | 6,900 | 39 |
| pLOI2184 | 2,100 | 12 | 2,400 | 39 |
| pLOI2164 | 3,200 | 20 | 6,900 | 74 |
| pLOI2307 | 6,600 | 28 | 13,000 | 60 |

[a]Plasmids pLOI2173 and pLOI2164 contain the celZ native promoter; pLOI2307 contains the strong promoter from pLOI2183. Plasmids pLOI2164 and pLOI2307 are pUC-based plasmids (high copy number). All other plasmids are derivatives of pST76-K (low copy number).
[b]Glucanase activities were determined after 16 h of growth at 30° C.
[c]Extracellular activity (secreted or released).

Recombinant hosts with low copy plasmids produced only 7–17% of the total EGZ extracellularly (after 16 h of growth) without the additional heterologous secretory proteins (out proteins encoded by plasmid pCPP2006). A larger fraction of EGZ (20–28%) was found in the extracellular broth surrounding host cells with the high-copy pUC-based plasmids than with the low copy pST76-based plasmids containing the same promoters. However, in either case, the addition of out genes encoding secretory proteins (e.g., pCPP2006) increased the total level of expression by up to 2-fold and increased the fraction of extracellular enzyme (38–74%) by approximately 4-fold. The highest activity, 13,000 IU/L of total glucanase of which 7,800 IU/L was found in the cell-free supernatant was produced by strain B having both pLOI2307 encoding celZ driven by a strong surrogate promoter and pCPP2006 encoding out secretory proteins).

It has been reported that under certain conditions (pH 7, 37° C.), the specific activity for pure EGZ enzyme is 419 IU (Py et al., (1991) *Protein Engineering* 4:325–333) and it has been determined that EGZ produced under these conditions is 25% more active than under the above-mentioned conditions (pH 5.2 citrate buffer, 35° C.). Accordingly, assuming a specific activity of 316 IU for pure enzyme at pH 5.2 (35° C.), the cultures of *E. coli* B (containing pLOI2307 and pCPP2006, e.g., plasmids encoding glucanase and secretory proteins), produced approximately 41 mg of active EGZ per liter or 4–6% of the total host cell protein was active glucanase.

Sequence Analysis of the Strongest Promoter Derived from *Z. mobilis*

The sequences of the four strongest surrogate promoters (pLOI2177, pLOI2180, pLOI2182, and pLOI2183) were determined. To facilitate this process, each was fused with pUC19 at the PstI site. The resulting plasmids, pLOI2196, pLOI2197, pLOI2198, and pLOI2199, were produced at high copy numbers (ColEI replicon) and could be sequenced in both directions using M13 and T7 sequencing primers. All four plasmids contained identical pieces of *Z. mobilis* DNA and were siblings. Each was 1417 bp in length and contained 4 internal Sau3AI sites. DNA and translated protein sequences (six reading frames) of each piece were compared to the current database. Only one fragment (281 bp internal fragment) exhibited a strong match in a Blast search (National Center for Biotechnology Information and this fragment was 99% identical in DNA sequence to part of the Z. mobilis hpnB gene which is proposed to function in cell envelope biosynthesis (Reipen et at, (1995) *Microbiology* 141:155–161). Primer extension analysis revealed a single major start site, 67 bp upstream from the Sau3AI/BamHI junction site with celZ, and a second minor start site further upstream (FIG. 5). Sequences in the −10 and −35 regions were compared to the conserved sequences for *E. coli* sigma factors (Wang et al., (1989) *J. Bacteriol.* 180:5626–5631; Wise et al., (1996)*J. Bacteriol.* 178:2785–2793). The dominant promoter region (approximately 85% of total start site) appears similar to a sigma$^{70}$ promoter while the secondary promoter site resembles a sigma$^{38}$ promoter.

Microscopic Analysis of Recombinant Host Cells Producing Glucanase

Figure 6:
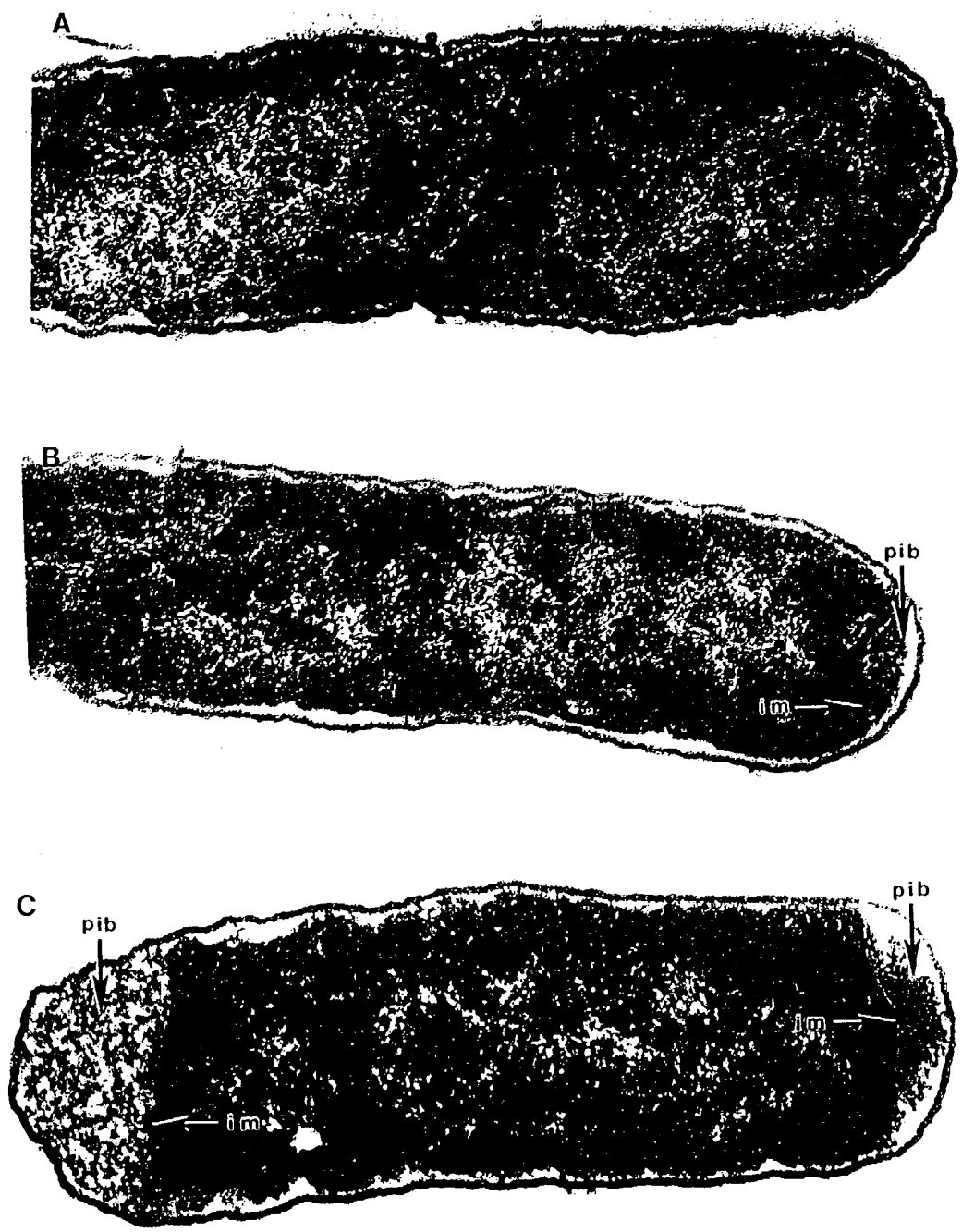
FIG. 6 represents electron micrographs of *E. coli* B cells harboring different plasmids expressing little if any (pUC19; panel A), moderate (pLOI2164; panel B), and high levels (pLOI2307; panel C) of glucanase in the form of periplasmic inclusion bodies (pib) localized between the outer cell wall and the inner membrane (im). The bar shown represents 0.1 μm.

Little difference in cell morphology was observed between recombinants and the parental organism by light microscopy. Under the electron microscope, however, small polar inclusion bodies were clearly evident in the periplasm of strain B (pLOI2164) expressing high amounts of glucanase and these inclusion bodies were presumed to contain EGZ (FIG. 6). In the strain B (pLOI2307) that produced 2-fold higher glucanase activity the inclusion bodies were even larger and occupied up to 20% of the total cell volume. The large size of these polar bodies suggests that glucanase activity measurements may underestimate the total EGZ production. Typically, polar inclusion bodies were smaller in host cells also having constructs encoding the out secretory proteins which allow for increased secretion of proteins from the periplasmic space. As expected, no periplasmic inclusion bodies were evident in the negative control strain B (pUC19) which does not produce glucanase.

EXAMPLE 2

Recombinant *Klebsiella* Hosts Suitable for Fermenting Oligosaccharides into Ethanol In this example, a recombinant *Klebsiella* host, suitable for use as a biocatalyst for depolymerizing and fermenting oligosaccharides into ethanol, is described.

Materials and Methods used in this Example

Unless otherwise stated, the following materials and methods were used in the example that follows.

Bacteria, Plasmids, and Culture Conditions

The strains and plasmids that were used in this exemplification are summarized in Table 4 below.

TABLE 4

Strains and Plasmids Used

| Strains/Plasmids | Properties | Sources/References |
|---|---|---|
| Strains | | |
| *Zymomonas mobilis* | | |
| CP4 | prototrophic | Ingram et al. (1988) Appl. Environ. Micro. 54: 397–404 |
| *Escherichia coli* | | |
| DH5α | lacZ M15 recA | Bethesda Research Laboratory |
| HB101 | recA lacY recA | ATCC37159 |
| *Klebsiella oxytoca* | | |
| M5A1 | prototrophic | Wood et al. (1992) Appl. Environ. Micro. 58: 2103–2110 |
| P2 | Pfl::pdc adhB cat | Wood et al. (1992) Appl. Environ. Micro. 58: 2103–2110 |
| SZ1 | pfl::pdc adhB cat; integrated celZ; tet | See text |
| SZ2 | pfl::pdc adhB cat; integrated celZ; tet | See text |
| SZ3 | pfl::pdc adhB cat; integrated celZ; tet | See text |
| SZ4 | pfl::pdc adhB cat; integrated celZ; tet | See text |
| SZ5 | pfl::pdc adhB cat; integrated celZ; tet | See text |
| SZ6 | pfl::pdc adhB cat; integrated celZ; tet | See text |
| SZ7 | pfl::pdc adhB cat; integrated celZ; tet | See text |
| SZ8 | pfl::pdc adhB cat; integrated celZ; tet | See text |
| SZ9 | pfl::pdc adhB cat; integrated celZ; tet | See text |
| SZ10 | pfl::pdc adhB cat; integrated celZ; tet | See text |
| Plasmids | | |
| pUC19 | bla cloning vector | New England Biolab |
| pBR322 | bla tet cloning vector | New England Biolab |
| pLOI1620 | bla celZ | Wood et al. (1997) Biotech. Bioeng. 55: 547–555 |
| pRK2013 | kan mobilizing helper plasmid (mob$^+$) | ATCC |
| pCPP2006 | Sp$^+$, 40 kbp fragment containing out genes from *E. chrysanthemi* EC16 | He et al. (1991) P.N.A.S. 88: 1079–1083 |
| pST76-K | kan low copy vector containing temperature sensitive pSC101 replicon | Posfai et al. (1997) J. Bact 179: 4426–4428 |
| pLOI2164 | bla celZ (BamHi eliminated from pLOI1620) | See text |
| pLOI2173 | kan celZ (native celZ promoter) | See text |
| pLOI2177 | kan celZ (surrogate promoter from Z. mobilis) | See text |
| pLOI2178 | kan celZ (surrogate promoter from Z. mobilis) | See text |

TABLE 4-continued

Strains and Plasmids Used

| Strains/Plasmids | Properties | Sources/References |
|---|---|---|
| pLOI2179 | kan celZ (surrogate promoter from Z. mobilis) | See text |
| pLOI2180 | kan celZ (surrogate promoter from Z. mobilis) | See text |
| pLOI2181 | kan celZ (surrogate promoter from Z. mobilis) | See text |
| pLOI2182 | kan celZ (surrogate promoter from Z. mobilis) | See text |
| pLOI2183 | kan celZ (surrogate promoter from Z. mobilis) | See text |
| pLOI2184 | kan celZ (surrogate promoter from Z. mobilis) | See text |
| pLOI2185 | kan celZ (surrogate promoter from Z. mobilis) | See text |
| pLOI2186 | kan celZ (surrogate promoter from Z. mobilis) | See text |
| pLOI2187 | kan celZ (surrogate promoter from Z. mobilis) | See text |
| pLOI2188 | kan celZ (surrogate promoter from Z. mobilis) | See text |
| pLOI2189 | kan celZ (surrogate promoter from Z. mobilis) | See text |
| pLOI2190 | kan celZ (surrogate promoter from Z. mobilis) | See text |
| pLOI2191 | kan celZ (surrogate promoter from Z. mobilis) | See text |
| pLOI2192 | kan celZ (surrogate promoter from Z. mobilis) | See text |
| pLOI2193 | kan celZ (surrogate promoter from Z. mobilis) | See text |
| pLOI2194 | kan celZ (surrogate promoter from Z. mobilis) | See text |
| pLOI2301 | AscI linker inserted into NdeI site of pUC19 | See text |
| pLOI2302 | AscI linker inserted into SapI site of pLOI2301 | See text |
| pLOI2303 | AvaI-EcoRI fragment from pBR322 inserted into PstI site of pLOI2302 after Klenow treatment | See text |
| pLOI2305 | EcoRI DNA fragment of K. oxytoca M5A1 genomic DNA (ca. 2.5 kb) cloned into the SinaI site of pLOI2303 | See text |
| pLOI2306 | EcoRI-SphI fragment from pLOI2183 cloned into EcoRI site of pLOI2305 | See text |

The culture conditions used for cultivating E. coli and K. oxytoca M5A1 typically employed Luria-Bertani broth (LB) containing per liter: 10 g Difco® tryptone, 5 g yeast extract, and 5 g sodium chloride, or, alternatively, Luria agar (LB supplemented with 15 g of agar) (Sambrook et al., (1989), Molecular Cloning: A Laboratory Manual, C.S.H.L., Cold Spring Harbor, N.Y.).

For screening bacterial colonies under selective conditions, CMC-plates (Luria agar plates containing 3 g L$^{-1}$ carboxymethyl cellulose) were used to determine levels of glucanase activity expressed by a given bacterial strain (Wood et al. (1988) Enzymology, 160:87–112). For cultivating ethanologenic strains, glucose was added to solid media (20 g L$^{-1}$) and broth (50 g L$^{-1}$). In determining glucanase activity, the glucose in the growth media was replaced with sorbitol (50 g L$^{-1}$), a non-reducing sugar. For cultivating various strains or cultures in preparation for introducing nucleic acids by electroporation, a modified SOC medium was used (e.g., 20 g L$^{-1}$ Difco® tryptone, 5 g L$^{-1}$, Difco® yeast extract, 10 mM NaCl, 2.5 mM KCl, 10 mM MgSO$_4$, 10 mM MgCl$_2$, and 50 g L$^{-1}$ glucose). The antibiotics ampicillin (50 mg L$^{-1}$), spectinomycin (100 mg L$^{-1}$), kanamycin (50 mg L$^{-1}$), tetracycline (6 or 12 mg L$^{-1}$), and chloramphenicol (40, 200, or 600 mg L$^{-1}$) were added when appropriate for selection of recombinant hosts bearing antibiotic resistance markers. Unless stated otherwise, cultures were grown at 37° C. Ethanologenic strains and strains containing plasmids with a temperature-sensitive pSC101 replicon were grown at 30° C.

Genetic Methods

Figure 7:
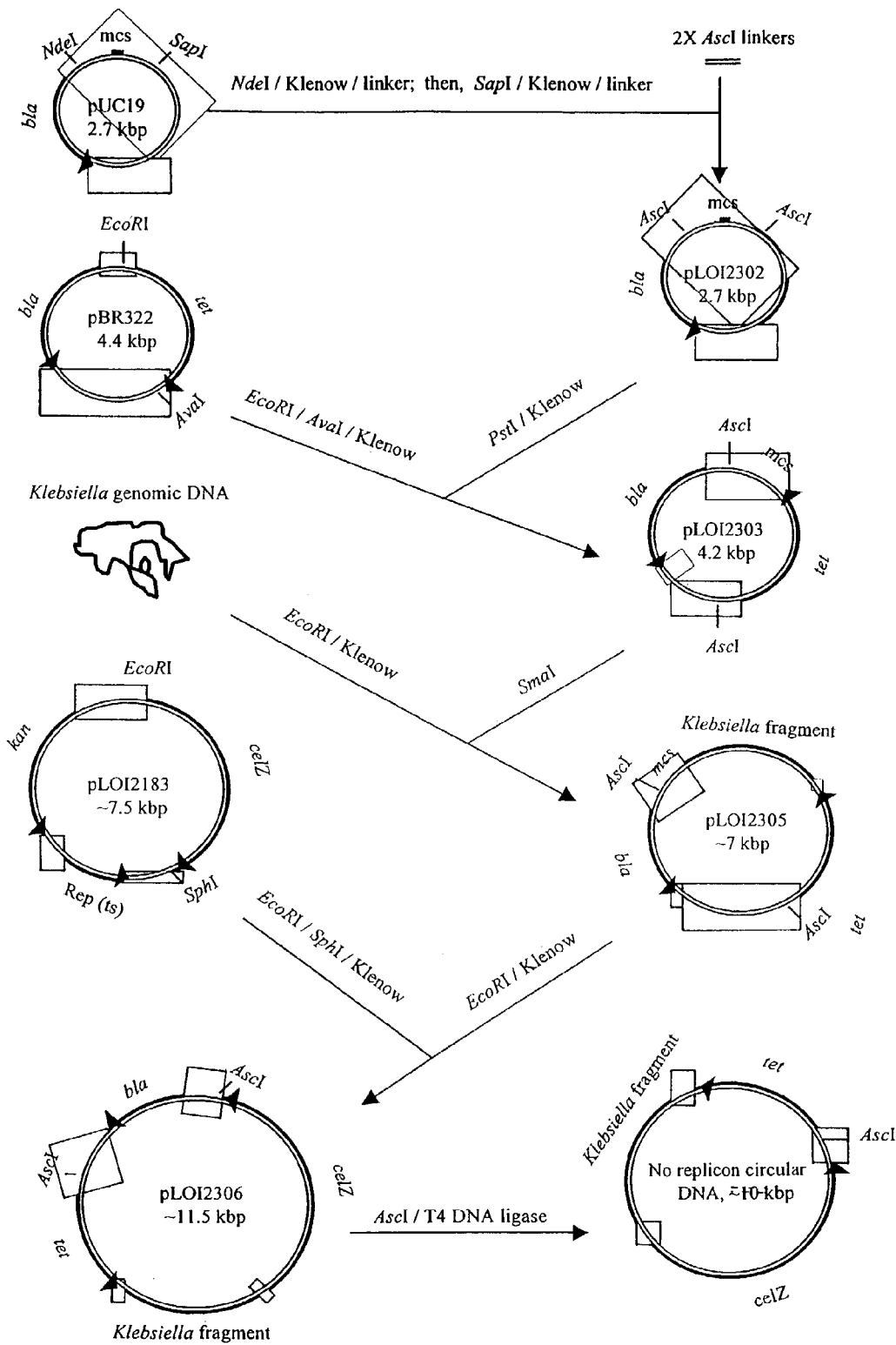
FIG. 7 shows a schematic detailing the cloning strategy used to construct the celZ integration vector pLOI2306, a genetic construct capable of being introduced into the genome of a recombinant host and conferring stable glucanase expression activity to the host.

For plasmid construction, cloning, and transformations, standard methods and E. coli DH5α hosts were used (Ausubel et al. (1987) Current Protocols in Molecular Biology. John Wiley & Sons, Inc.; Sambrook et al, (1989) Molecular Cloning: A Laboratory Manual, C.S.H.L., Cold Spring Harbor, N.Y.). Construction of the celZ integration vector, pLOI2306, was performed as shown in FIG. 7. A circular DNA fragment lacking a replicon from pLOI2306 (see FIG. 7) was electroporated into the ethanologenic K. oxytoca P2 using a Bio-Rad Gene Pulser using the following conditions: 2.5 kV and 25 µF with a measured time constant of 3.8–4.0 msec (Comaduran et al (1998) Biotechnol. Lett. 20:489–493). The E. chrysanthemi EC 16 secretion system (pCPP2006) was conjugated into K. oxytoca using pRK2013 for mobilization (Murata et al (1990) J. Bacteriol. 172: 2970–2978). Small scale and large scale plasmid isolations were performed using the TELT procedure and a Promega Wizard Kit, respectively. DNA fragments were isolated from gels using a Qiaquick® Gel Extraction Kit from Qiagen® (Qiagen Inc., Chatsworth, Calif.). Chromosomal DNA from

*K. oxytoca* M5A1 and *Z. mobilis* CP4 were isolated as described by Cutting and Yomano (see Example 1). The DNAs of interest were sequenced using a LI-COR Model 4000-L DNA sequencer (Wood et al. (1997) *Biotech. Bioeng.* 55:547–555).

Chromosomal Integration of celZ

Two approaches were employed for chromosomal integration of celZ, using selection with a temperature-conditional plasmid (pLOI2183) using a procedure previously described for *E. coli* (Hamilton et al., (1989) *J. Bacteriol.* 171:4617–4622) and direct integration of circular DNA fragments lacking a functional replicon. This same method was employed for chromosomal integration of *Z. mobilis* genes encoding the ethanol pathway in *E. coli* B (Ohta K et al., (1991) *Appl. Environ. Microbiol.* 57:893–900) and *K. oxytoca* M5A1 (Wood et al. (1992) *Appl. Environ. Microbiol.* 58:2103–2110). Typically, circular DNA was transformed into P2 by electroporation using a Bio-Rad Gene Pulser. Next, transformants were selected on solid medium containing tetracycline (6 mg $L^{-1}$) and grown on CMC plates to determine levels of glucanase activity.

Glucanase Activity

Glucanase activity resulting from expression of celZ gene product (i.e., glucanase) under the control of different test promoters was evaluated by staining CMC plates as described in Example 1. This calorimetric assay results in yellow zones indicating glucanase activity and the diameter of the zone was used as a relative measure of celZ polypeptide expression. Clones that exhibited the largest zones of yellow color were further evaluated for glucanase activity at 35° C. using carboxymethyl cellulose as the substrate (20 g $L^{-1}$ dissolved in 50 mM citrate buffer, pH 5.2) (Wood et al. (1988) *Methods in Enzymology* 160: 87–112). In order to measure the amount of intracellular glucanase, enzymatic activity was released from cultures by treatment with ultrasound for 4 seconds (Model W-290F cell disrupter, Heat System-Ultrasonics Inc., Plainview, N.Y.). The amount of glucanase activity expressed was measured and is presented here as µmol of reducing sugar released per min (IU). Reducing sugar was measured as described by Wood (Wood et al. (1988) *Methods in Enzymology* 160: 87–112) using a glucose standard.

Substrate Depolymerization

To further determine the amount of glucanase activity produced by various host cells, different carbohydrate substrates were incubated with various cell extracts (20 g $L^{-1}$ suspended in 50 mM citrate buffer, pH 5.2). In one example, test substrates comprising acid-swollen cellulose and ball-milled cellulose were prepared as described by Wood (Wood et al. (1988) *Methods in Enzymology* 160: 87–112). A typical polysaccharase extract (i.e., EGZ (glucanase) from *K. oxytoca* SZ6 (pCPP2006)) was prepared by cultivating the host cells at 30° C. for 16 h in LB supplemented with sorbitol, a nonreducing sugar. Dilutions of cell-free broth were added to substrates and incubated at 35° C. for 16 h. Several drops of chloroform were added to prevent the growth of adventitious contaminants during incubation. Samples were removed before and after incubation to measure reducing sugars by the DNS method (see, Wood et al (1988) *Methods in Enzymology* 160: 87–112). The degree of polymerization (DP) was estimated by dividing the total calculated sugar residues present in the polymer by the number of reducing ends.

Fermentation Conditions

Fermentations were carried out in 250 ml flasks containing 100 ml of Luria broth supplemented with 50 g $L^{-1}$ of carbohydrate. Test carbohydrates were sterilized separately and added after cooling. To minimize substrate changes, acid-swollen cellulose, ball-milled cellulose and xylan were not autoclaved. The antibiotic chloramphenicol (200 mg $L^{-1}$) was added to prevent the growth of contaminating organisms. Flasks were inoculated (10% v/v) with 24-h broth cultures (50 g $L^{-1}$ glucose) and incubated at 35° C. with agitation (100 rpm) for 24–96 h. To monitor cultures, samples were removed daily to determine the ethanol concentrations by gas chromatography (Dombek et al (1986) *Appl. Environ. Microbiol.* 52:975–981).

Methods for Isolating and Identifying a Surrogate Promoter

In order to identify random fragments of *Z. mobilis* that would serve as surrogate promoters for the expression of heterologous genes in *Klebsiella* and other host cells, a vector for the efficient cloning of candidate promoters was constructed as described in Example 1 (see also, Ingram et al (1988) *Appl. Environ. Microbiol* 54:397–404).

Next, Sau3AI digested *Z. mobilis* DNA fragments were ligated into the BamHI site of pLOI2171 to generate a library of potential promoters. These plasmids were transformed into *E. coli* DH5α for initial screening. Of the 18,000 colonies individually tested on CMC plates, 75 clones produced larger yellow zones than the control (pLOI2173). Plasmids from these 75 clones were then transformed into *K. oxytoca* M5A1, retested, and found to express high levels of celZ in this second host.

Recombinant *Klebsiella* Hosts for Producing Polysaccharase

The high expressing clones (pLOI2177 to pLOI2194) with the largest zones on CMC plates indicating celZ expression were grown in LB broth and assayed for glucanase activity (Table 5).

TABLE 5

Evaluation of promoters for celZ expression and secretion in *K. oxytoca* M5A1

| Plasmids[a] | No secretion genes | | Secretion genes present (pCPP2006) | |
|---|---|---|---|---|
| | Total activity (IU $L^{-1}$)[b] | Secreted activity (IU $L^{-1}$) | Total activity (IU $L^{-1}$) | Secreted activity (IU $L^{-1}$) |
| pLOI2173 | 2,450 | 465 | 3,190 | 1,530 |
| pLOI2177 | 19,700 | 3,150 | 32,500 | 13,300 |
| pLOI2178 | 15,500 | 2,320 | 21,300 | 11,500 |
| pLOI2179 | 15,400 | 2,310 | 21,400 | 12,000 |
| pLOI2180 | 21,400 | 3,210 | 30,800 | 13,600 |
| pLOI2181 | 15,600 | 2,490 | 21,000 | 11,800 |
| pLOI2182 | 19,600 | 3,130 | 31,100 | 14,000 |
| pLOI2183 | 20,700 | 3,320 | 32,000 | 14,000 |
| pLOI2184 | 15,500 | 2,480 | 21,200 | 11,900 |
| pLOI2185 | 15,100 | 2,420 | 24,600 | 11,500 |
| pLOI2186 | 17,000 | 2,380 | 25,700 | 13,400 |
| pLOI2187 | 15,800 | 2,210 | 24,500 | 12,200 |
| pLOI2188 | 18,200 | 2,180 | 25,600 | 12,000 |
| pLOI2189 | 14,800 | 2,360 | 27,100 | 12,700 |
| pLOI2190 | 16,100 | 2,410 | 26,500 | 12,500 |
| pLOI2191 | 15,800 | 2,210 | 25,000 | 12,400 |
| pLOI2192 | 15,100 | 1,810 | 24,900 | 12,500 |
| pLOI2193 | 16,700 | 2,010 | 24,600 | 12,800 |
| pLOI2194 | 15,400 | 2,770 | 21,500 | 11,900 |

[a]pLOI2173 contains the celZ gene with the original promoter, all others contain the celZ gene with a *Z. mobilis* DNA fragment which serves as a surrogate promoter.
[b]Glucanase (CMCase) activities were determined after 16 h of growth at 30° C.

Activities with these plasmids were up to 8-fold higher than with the control plasmid containing a native celZ promoter (pLOI2173). The four plasmids which produced the largest zones (pLOI2177, pLOI2180, pLOI2182 and pLOI2183) also produced the highest total glucanase activities (approximately 20,000 IU $L^{-1}$) released into the broth. One of these plasmids, pLOI2183, was selected for chromosomal integration.

Chromosomal Integration of a Polysaccharase Gene

To stably incorporate a desirable polysaccharase gene into a suitable host cell, e.g., *Klebsiella* P2 strain, a novel vector (pLOI2306) was constructed to facilitate the isolation of a DNA fragment which lacked all replication functions but contained the celZ gene with surrogate promoter, a selectable marker, and a homologous DNA fragment for integration (FIG. 7). Two AscI sites were added to pUC19 by inserting a linker (GGCGCGCC; SEQ ID NO: 11) into Klenow-treated NdeI and SapI sites which flank the polylinker region to produce pLOI2302. A blunt fragment containing the tet resistance marker gene from pBR322 (excised with EcoRI and AvaI, followed by Klenow treatment) was cloned into the PstI site of pLOI2302 (cut with PstI, followed by Klenow treatment) to produce pLOI2303. To this plasmid was ligated a blunt fragment of *K oxytoca* M5A1 chromosomal DNA (cut with EcoRI and made blunt with Klenow treatment) into the SmaI site of pLOI2303 to produce (pLOI2305). The EcoRI-SphI fragment (Klenow treated) containing the surrogate *Z. mobilis* promoter and celZ gene from pLOI2183 was ligated into the EcoRI site of pLOI2305 (EcoRI, Klenow treatment) to produce pLOI2306. Digestion of pLOI2306 with AscI produced two fragments, the larger of which contained the celZ gene with a surrogate promoter, tet gene, and chromosomal DNA fragment for homologous recombination. This larger fragment (10 kbp) was purified by agarose gel electrophoresis, circularized by self-ligation, and electroporated into the *Klebsiella* strain P2 and subsequently grown under selection for tetracycline resistance. The resulting 21 tetracycline-resistant colonies were purified and tested on CMC plates for glucanase activity. All were positive with large zones indicating functional expression of the celZ gene product.

Clones used to produce the recombinant strains were tested for the presence of unwanted plasmids by transforming DH5α with plasmid DNA preparations and by gel electrophoresis. No transformants were obtained with 12 clones tested. However, two of these strains were subsequently found to contain large plasmid bands which may contain celZ and these were discarded. Both strains with large plasmids contained DNA which could be sequenced with T7 and M13 primers confirming the presence of multicopy plasmids. The remaining ten strains contain integrated celZ genes and could not be sequenced with either primer.

Figure 8:
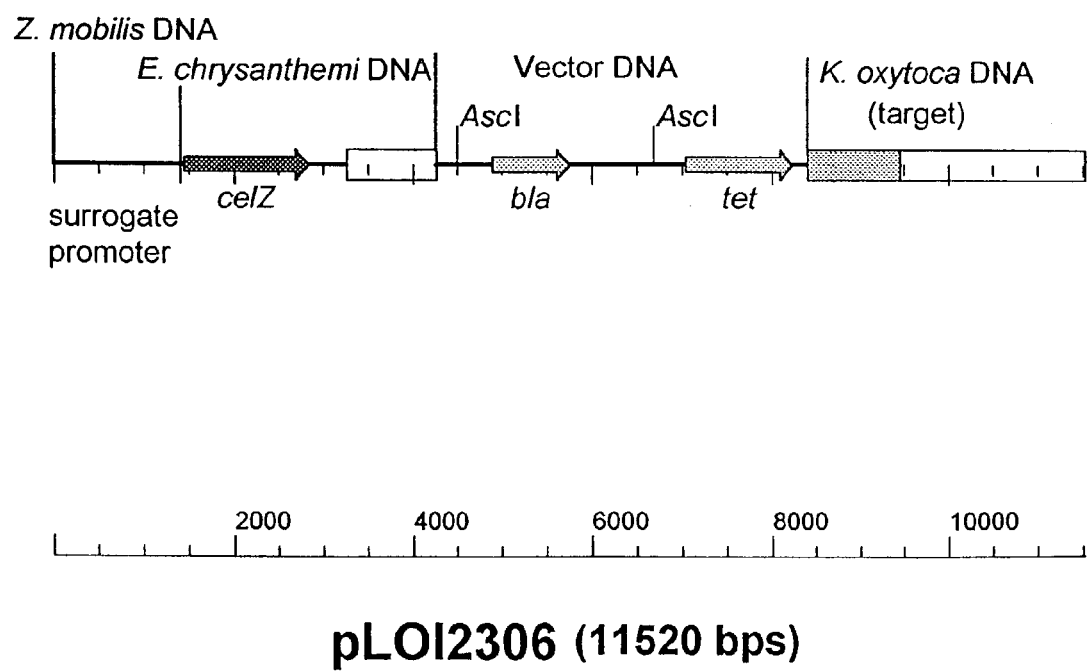
FIG. 8 shows a schematic representation of the celZ integration vector pLOI2306 (SEQ ID NO: 12) with the locations of the surrogate promoter from *Z. mobilis*, the celZ gene from *E. chrysanthemi*, resistance markers (bla and tet), and *K. oxytoca* target sequence indicated.

The structural features of the novel vector pLOI2306 are schematically shown in FIG. 8 and the nucleotide sequence of the vector, including various coding regions (i.e., of the genes celZ, bla, and tet), are indicated in SEQ ID NO: 12 of the sequence listing. Nucleotide base pairs 3282–4281, which represent non-coding sequence downstream of the celZ gene (obtained from *E. chrysanthemi*), and base pairs 9476–11544 which represent a portion of the non-coding target sequence obtained from *K. oxytoca* M5A1, remain to be sequenced using standard techniques (e.g., as described in Sambrook, J. et al., T. *Molecular Cloning: A Laboratory Manual.* 2nd, ed., Cold Spring Harbor Laboratory, Cold Spring Harbor Laboratory Press, Cold Spring Harbor, N.Y., (1989); *Current Protocols in Molecular Biology*, eds. Ausubel et al., John Wiley & Sons (1992)). For example, sufficient flanking sequence on either side of the aforementioned unsequenced regions of the pLOI2306 plasmid is provided such that sequencing primers that correspond to these known sequences can be synthesized and used to carry out standard sequencing reactions using the pLOI2306 plasmid as a template.

Alternatively, it will be understood by the skilled artisan that these unsequenced regions can also be determined even in the absence of the pLOI2306 plasmid for use as a template. For example, the remaining celZ sequence can be determined by using the sequence provided herein (e.g., nucleotides 1452–2735 of SEQ ID NO: 12) for synthesizing probes and primers for, respectively, isolating a celZ containing clone from a library comprising *E. chrysanthemi* sequences and sequencing the isolated clone using a standard DNA sequencing reaction. Similarly, the remaining target sequence can be determined by using the sequence provided herein (e.g., nucleotides 8426–9475 of SEQ ID NO: 12) for synthesizing probes and primers for, respectively, isolating a clone containing target sequence from a library comprising *K. oxytoca* M5A1 EcoRI fragments (e.g., of the appropriate size) and sequencing the isolated clone using a standard DNA sequencing reaction (a source of *K. oxytoca* M5A1 would be, e.g., ATCC 68564 cured free of any plasmid using standard techniques). The skilled artisan will further recognize that the making of libraries representative of the cDNA or genomic sequences of a bacterium and the isolation of a desired nucleic acid fragment from such a library (e.g., a cDNA or genomic library), are well known in the art and are typically carried out using, e.g., hybridization techniques or the polymerase chain reaction (PCR) and all of these techniques are standard in the art (see, e.g., Sambrook, J. et al., T. *Molecular Cloning: A Laboratory Manual.* 2nd, ed., Cold Spring Harbor Laboratory, Cold Spring Harbor Laboratory Press, Cold Spring Harbor, N.Y., (1989); *Current Protocols in Molecular Biology*, eds. Ausubel et al., John Wiley & Sons (1992); *Oligonucleotide Synthesis* (M. J. Gait, Ed. 1984); and *PCR Handbook Current Protocols in Nucleic Acid Chemistry*, Beaucage, Ed. John Wiley & Sons (1999) (Editor)).

Heterologous Gene Expression Using a Surrogate Promoter and Integrated or Plasmid-Based Constructs The ten integrated strains (SZ1–SZ10) were investigated for glucanase production in LB sorbitol broth (Table 6). All produced 5,000–7,000 $IUL^{-1}$ of active enzyme. Although this represents twice the activity expressed from plasmid pLOI2173 containing the native celZ promoter, the integrated strains produced only ⅓ the glucanase activity achieved by P2 (pLOI2183) containing the same surrogate *Z. mobilis* promoter (Table 5). The reduction in glucanase expression upon integration may be attributed to a decrease in copy number (i.e., multiple copy plasmid versus a single integrated copy).

Secretion of Glucanase EGZ

*K. oxytoca* contains a native Type II secretion system for pullulanase secretion (Pugsley (1993) *Microbiol. Rev.* 57:50–108), analogous to the secretion system encoded by the out genes in *Erwinia chrysanthemi* which secrete pectate lyases and glucanase (EGZ) (Barras et al. (1994) *Annu. Rev. Phytopathol.* 32:201–234; He et al. (1991) *Proc. Natl. Acad. Sci. USA.* 88: 1079–1083). Type II secretion systems are typically very specific and function poorly with heterologous proteins (He et al. (1991) *Proc. Natl. Acad. Sci. USA.* 88: 1079–1083; Py et al. (1991) *FEMS Microbiol. Lett.* 79:315–322; Sauvonnet et al. (1996) *Mol. Microbiol.* 22: 1–7). Thus as expected, recombinant celZ was expressed primarily as a cell associated product with either M5A1 (Table 5) or P2 (Table 6) as the host. About ¼ (12–26%) of the total recombinant EGZ activity was recovered in the broth. With *E. coli* DH5α, about 8–12% of the total extracellular EGZ was present. Thus the native secretion system in *K. oxytoca* may facilitate partial secretion of recombinant EGZ.

To further improve secretion of the desired products, type II secretion genes (out genes) from *E. chrysanthemi* EC16 were introduced (e.g., using pCPP2006) to facilitate secretion of the recombinant EGZ from strain P86021 in ethanologenic strains of K. oxytoca (Table 5 and Table 6). For most strains containing plasmids with celZ, addition of the out genes resulted in a 5-fold increase in extracellular EGZ and a 2-fold increase in total glucanase activity. For strains with integrated celZ, addition of the out genes resulted in a 10-fold increase in extracellular EGZ and a 4-fold increase in total glucanase activity. In both cases, the out genes facilitated secretion of approximately half the total glucanase activity. The increase in EGZ activity resulting from addition of the out genes may reflect improved folding of the secreted product in both plasmid and integrated celZ constructs. The smaller increase observed with the pUC-based derivatives may result from plasmid burden and competition for export machinery during the production of periplasmic β-lactamase from the bla gene on this high copy plasmid.

Two criteria were used to identify the best integrated strains of P2, growth on solid medium containing high levels of chloramphenicol (a marker for high level expression of the upstream pdc and adhB genes) and effective secretion of glucanase with the out genes. Two recombinant strains were selected for further study, SZ2 and SZ6. Both produced 24,000 $IU^{L-1}$ of glucanase activity, equivalent to approximately 5% of the total cellular protein (Py et al. (1991) Protein Engin. 4:325–333).

Substrate Depolymerization

The substrate depolymerization of the recombinant EGZ was determined to be excellent when applied to a CMC source (Table 7). When applied to acid swollen cellulose, the activity of the glucanase was less than 10% of the activity measured for CMC activity. Little activity was noted when the polysaccharase was applied to Avicel or xylan. However, when allowed to digest overnight, the EGZ polysaccharase resulted in a measurable reduction in average polymer length for all substrates. CMC and acid-swollen cellulose were depolymerized to an average length of 7 sugar residues. These cellulose polymers of 7 residues are marginally soluble and, ideally, may be further digested for efficient metabolization (Wood et al. (1992) Appl. Environ. Microbiol. 58:2103–2110). The average chain length of ball-milled cellulose and Avicel was reduced to ⅓ of the original length while less than a single cut was observed per xylan polymer.

TABLE 6

Comparison of culture growth, glucanase production, and secretion from ethanologenic K. oxytoca strains containing integrated celZ

| Strains | Growth on solid medium (600 mg $L^{-1}$CM) | Glucanase production and secretion (IU $L^{-1}$) | | | |
|---------|---------|---------|---------|---------|---------|
| | | No secretion system | | Adding secretion system (pCPP2006) | |
| | | Total activity | Secreted activity | Total activity | Secreted activity |
| P2 | ++++ | 0 | 0 | 0 | 0 |
| SZ1 | ++ | 6,140 | 1,600 | 26,100 | 14,300 |
| SZ2 | ++++ | 6,460 | 1,160 | 23,700 | 11,400 |
| SZ3 | +++ | 5,260 | 1,320 | 18,400 | 8,440 |
| SZ4 | +++ | 7,120 | 1,070 | 23,200 | 9,990 |
| SZ5 | + | 6,000 | 1,080 | 29,300 | 15,500 |
| SZ6 | ++++ | 7,620 | 1,520 | 24,300 | 11,900 |
| SZ7 | + | 6,650 | 1,330 | 28,800 | 15,500 |
| SZ8 | +++ | 7,120 | 854 | 28,700 | 14,900 |
| SZ9 | ++ | 7,530 | 1,130 | 26,700 | 12,800 |
| SZ10 | +++ | 4,940 | 939 | 17,000 | 6,600 |

Glucanase (CMCase) activities were determined after 16 h of growth at 30° C.

TABLE 7

Depolymerization of various substrates by EGZ from cell free broth of strain SZ6 (pCPP2006)

| Substrates | Enzyme activity (IU/L) | Estimated degree of polymerization | |
|---------|---------|---------|---------|
| | | Before digestion | After digestion |
| Carboxymethyl cellulose | 13,175 | 224 | 7 |
| Acid-Swollen cellulose | 893 | 87 | 7 |
| Ball-milled cellulose | 200 | 97 | 28 |
| Avicel | 41 | 104 | 35 |
| Xylan from oat spelts | 157 | 110 | 78 |

Strain SZ6 (pCPP2006) was grown in LB-sorbitol broth for 16 h as a source of secreted EGZ.

Fermentation

To be useful, addition of celZ and out genes to strain P2 must not reduce the fermentative ability of the resulting biocatalyst. A comparison was made using glucose and cellobiose (Table 8). All strains were equivalent in their ability to ferment these sugars indicating a lack of detrimental effects from the integration of celZ or addition of pCPP2006. These strains were also examined for their ability to convert acid-swollen cellulose directly into ethanol. The most active construct SZ6 (pCPP2006) produced a small amount of ethanol (3.9 g $L^{-1}$) from amorphous cellulose. Approximately 1.5 g $L^{-1}$ ethanol was present initially at the time of inoculation for all strains. This decreased with time to zero for all strains except SZ6 (pCPP2006). Thus the production of 3.9 g $L^{-1}$ ethanol observed with SZ6 (pCPP2006) may represent an underestimate of total ethanol production. However, at best, this represents conversion of only a fraction of the polymer present. It is likely that low levels of glucose, cellobiose, and cellotriose were produced by EGZ hydrolysis of acid swollen cellulose and fermented. These compounds can be metabolized by the native phosphoenolpyruvate-dependent phosphotransferase system in K. oxytoca (Ohta K et al., (1991) Appl. Environ. Microbiol. 57:893–900; Wood et al. (1992) Appl. Environ. Microbiol. 58:2103–2110).

TABLE 8

Ethanol production by strain SZ6 containing out genes (pCPP2006) and integrated celZ using various substrates (50 g $L^{-1}$)

| Strains | Ethanol production (g $L^{-1}$) | | |
|---------|---------|---------|---------|
| | Glucose | Cellobiose | Acid-swollen cellulose |
| P2 | 22.9 | 22.7 | 0 |
| P2 (pCPP2006) | 22.6 | 21.3 | 0 |
| SZ6 | 21.5 | 19.7 | 0 |
| SZ6 (pCPP2006) | 22.7 | 21.2 | 3.9 |

Initial ethanol concentrations at the time of inoculation were approximately 1.5 g $L^{-1}$ for all cultures. With acid swollen cellulose as a substrate, these levels declined to 0 after 72 h of incubation for all strains except SZ6 (pCP206).

Equivalents

Those skilled in the art will recognize, or be able to ascertain using no more than routine experimentation, many equivalents to the specific embodiments of the invention described herein. Such equivalents are intended to be encompassed by the following claims. Moreover, any number of genetic constructs, host cells, and methods described in U.S. Pat. Nos. 5,821,093; 5,482,846; 5,424,202; 5,028,539; 5,000,000; 5,487,989, 5,554,520, and 5,162,516, may be employed in carrying out the present invention and are hereby incorporated by reference.

---

What is claimed is:

1. A recombinant host cell comprising:
a first heterologous polynucleotide segment comprising a sequence encoding a polysaccharase under the transcriptional control of a surrogate promoter comprising the polynucleotide sequence of SEQ ID NO: 1 or 2, or a fragment thereof, wherein said promoter causes increased expression of said polysaccharase as compared to expression of said polysaccharase under transcriptional control of its native promoter; and
a second heterologous polynucleotide segment comprising a sequence encoding a secretory polypeptide, wherein expression of said first and second polynucleotide segments results in increased production of said polysaccharase by the recombinant host cell as compared to production of said polysaccharase under transcriptional control of its native promoter and in the absence of expression of said second polynucleotide segment.

2. The recombinant host cell of claim 1 wherein said increased production comprises an increase in activity of said polysaccharase, in amount of said polysaccharase or a combination of increase in activity and increase in amount.

3. The recombinant host cell of claim 2 wherein said polysaccharase polypeptide is secreted.

4. The recombinant host cell of claim 1 wherein said host cell is a bacterial cell.

5. The recombinant host cell of claim 4 wherein said host cell is a Gram-negative bacterial cell.

6. The recombinant host cell of claim 5 wherein said host cell is a facultatively anaerobic bacterial cell.

7. The recombinant host cell of claim 6 wherein said host cell is selected from the family Enterobacteriaceae.

8. The recombinant host cell of claim 7 wherein said host is selected from the group consisting of *Escherichia* and *Klebsiella*.

9. The recombinant host cell of claim 8 wherein said *Escherichia* is selected from the group consisting of *E. coli* B (ATCC 11303), *E. coli* DH5α, *E. coli* KO4 (ATCC 55123), *E. coli* KO11 (ATCC 55124), *E. coli* KO12 (ATCC 55125) and *E. coli* LY01 (ATCC PTA-3466), *K. oxytoca* M5A1 (ATCC 68564), and *K. oxytoca* P2 (ATCC 55307).

10. The recombinant host cell of claim 1 wherein said polysaccharase is selected from the group consisting of glucanase, endoglucanase, exoglucanase, cellobiohydrolase, β-glucosidase, endo-1,4-β-xylanase, α-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase and a combination thereof.

11. The recombinant host cell of claim 10 wherein said polysaccharase is glucanase.

12. The recombinant host cell according to claim 10, wherein said polysaccharase is an expression product of a celZ gene.

13. The recombinant host cell of claim 12 wherein said celZ gene is derived from *Erwinia chrysanthemi*.

14. The recombinant host cell of claim 2 wherein said second heterologous polynucleotide segment comprises at least one pul gene or out gene.

15. The recombinant host cell of claim 2 wherein said second heterologous polynucleotide segment is derived from a bacterial cell selected from the family Enterobacteriaceae.

16. The recombinant host cell of claim 15 wherein said bacterial cell is selected from the group consisting of *K. oxytoca, E. carotovora, E. carotovora* subspecies *carotovora, E. carotovora* subspecies *atroseptica,* and *E. chrysanthemi*.

17. The recombinant host cell of claim 1 wherein said surrogate promoter comprises a polynucleotide fragment derived from *Zymomonas mobilis*.

18. The recombinant host cell of claim 1 wherein said host cell is ethanologenic.

19. A recombinant ethanologenic host cell comprising a heterologous polynucleotide segment encoding a polysaccharase under the transcriptional control of a surrogate promoter comprising the polynucleotide sequence of SEQ ID NO: 1 or 2, or a fragment thereof, wherein said promoter causes increased expression of said polysaccharase, as compared to expression of said polysaccharase under transcriptional control of its native promoter.

20. The recombinant host cell of claim 19 wherein said host cell is a bacterial cell.

21. The recombinant host cell of claim 20 wherein said host cell is a Gram-negative bacterial cell.

22. The recombinant host cell of claim 21 wherein said host cell is a facultatively anaerobic bacterial cell.

23. The recombinant host cell of claim 22 wherein said host cell is selected from the family Enterobacteriaceae.

24. The recombinant host cell of claim 23 wherein said host is selected from the group consisting of *Escherichia* and *Klebsiella*.

25. The recombinant host cell of claim 24 wherein said *Escherichia* and *Klebsiella* selected from the group consisting of *E. coli* B (ATCC 11303), *E. coli* DH5α, *E. coli* KO4 (ATCC 55123), *E. coli* KO11 (ATCC 55124), *E. coli* KO12 (ATCC 55125) and *E. coli* LY01 (ATCC PTA-3466), *K. oxytoca* M5A1 (ATCC 68564), and *K. oxytoca* P2 (ATCC 55307).

26. The recombinant host cell of claim 19 wherein said polysaccharase is selected from the group consisting of glucanase, endoglucanase, exoglucanase, cellobiohydrolase, α-glucosidase, endo-1,4-α-xylanase, β-xylosidase, β-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase and a combination thereof.

27. The recombinant host cell of claim 26 wherein said polysaccharase is a glucanase.

28. The recombinant host cell according to claim 27 wherein said polysaccharase is an expression product of a celZ gene.

29. The recombinant host cell of claim 28 wherein said celZ gene is derived from *Erwinia chrysanthemi*.

30. The recombinant host cell of claim 19 wherein said surrogate promoter comprises a polynucleotide fragment derived from *Zymomonas mobilis*.

31. A recombinant ethanologenic Gram-negative bacterial host cell comprising:
a first heterologous polynucleotide segment comprising a sequence encoding a first polypeptide under the transcriptional control of a surrogate promoter comprising the polynucleotide sequence of SEQ ID NO: 1 or 2, or a fragment thereof, wherein said promoter causes increased expression of said polysaccharase as compared to expression of said polysaccharase under transcriptional control of its native promoter; and
a second heterologous polynucleotide segment comprising a sequence encoding a secretory polypeptide, wherein expression of said first and second polynucleotide segments results in increased production of the first polypeptide by the host cell as compared to production of said first polypeptide under transcriptional control of its native promoter and in the absence of expression of said second polynucleotide segment.

32. The recombinant host cell of claim 31 wherein said first polypeptide is secreted.

33. The recombinant host cell of claim 31 wherein said host cell is a facultatively anaerobic bacterial cell.

34. The recombinant host cell of claim 33 wherein said host cell is selected from the family Enterobacteriaceae.

35. The recombinant bacterial host cell of claim 34 wherein said host cell is selected from the group consisting of *Escherichia* and *Klebsiella*.

36. The recombinant bacterial host cell of claim 35 wherein said *Escherichia* and *Klebsiella* are selected from the group consisting of *E. coli* B (ATCC 11303), *E. coli* DH5α, *E. coli* KO4 (ATCC 55123), *E. coli* KO11 (ATCC 55124), *E. coli* KO12 (ATCC 55125) and *E. coli* LY01 (ATCC PTA-3466), *K. oxytoca* M5A1 (ATCC 68564), and *K. oxytoca* P2 (ATCC 55307).

37. The recombinant bacterial host cell of claim 31 wherein said first polypeptide is a polysaccharase.

38. The recombinant bacterial host cell of claim 37 wherein said polysaccharase is of increased activity.

39. The recombinant host cell of claim 37 wherein said polysaccharase is selected from the group consisting of glucanase, endoglucanase, exoglucanase, cellobiohydrolase, alpha.-glucosidase, endo-1,4-alpha-xylanase, beta-xylosidase, beta.-glucuronidase, alpha-L-arabinofuranosidase, acetylesterase, acetylxylanesterase, alpha-amylase, beta.-amylase, glucoamylase, pullulanase, beta-glucanase, hemicellulase, arabinosidase, mannanase, pectin hydrolase, pectate lyase, or a combination thereof.

40. The recombinant host cell of claim 39 wherein said polysaccharase is glucanase.

41. The recombinant host cell according to claim 40 wherein said glucanase is an expression product of a celZ gene.

42. The recombinant host cell of claim 41 wherein said celZ gene is derived from *Erwinia chrysanthemi*.

43. The recombinant host cell of claim 31 wherein said second heterologous polynucleotide segment comprises at least one pul gene or out gene.

44. The recombinant host cell of claim 43 wherein said second heterologous polynucleotide segment is derived from a bacterial cell selected from the family Enterobacteriaceae.

45. The recombinant host cell of claim 44 wherein said bacterial cell is selected from the group consisting of *K. oxytoca, E. carotovora, E. carotovora* subspecies *carotovora, E. carotovora* subspecies *atroseptica,* and *E. chrysanthemi.*

46. A method for enzymatically degrading an oligosaccharide comprising the steps of:
providing a oligosaccharide; and
contacting said oligosaccharide with a recombinant host cell according to claim 1,
wherein expression of said first and second polynucleotide segments results in the increased production of polysaccharase activity by the recombinant host cell such that the oligosaccharide is enzymatically degraded.

47. The method of claim 46 wherein said polysaccharase is secreted.

48. The method of claim 46 wherein said host cell is ethanologenic.

49. The method of claim 46 wherein said method is conducted in an aqueous solution.

50. The method of claim 46 wherein said method is used for simultaneous saccharification and fermentation.

51. The method of claim 46 wherein said oligosaccharide is selected from the group consisting of lignocellulose, hemicellulose, cellulose, pectin, and any combination thereof.

52. A method of making a recombinant host cell for use in simultaneous saccharification and fermentation comprising:
introducing into said host cell a first heterologous polynucleotide segment comprising a sequence encoding a polysaccharase under the transcriptional control of a surrogate promoter comprising the polynucleotide sequence of SEQ ID NO: 1 or 2, a fragment thereof, wherein said promoter causes increased expression of said polysaccharase as compared to expression of said polysaccharase under transcriptional control of its native promoter; and
introducing into said host cell a second heterologous polynucleotide segment comprising a sequence encoding a secretory polypeptide;
wherein expression of said first and second polynucleotide segments results in increased production of said polysaccharase by the recombinant host cell as compared to production of said polysaccharase under transcriptional control of its native promoter and in the absence of expression of said second polynucleotide segment.

53. The method of claim 52 wherein said increased production comprises an increase in activity of said polysaccharase, in amount of said polysaccharase or a combination of increase in activity and increase in amount.

54. The recombinant host cell of claim 52 wherein said polysaccharase polypeptide is secreted.

55. The method of claim 52 or 54 wherein said host cell is ethanologenic.

56. A vector comprising plasmid pLOI2306, wherein said plasmid comprises the polynucleotide sequence of SEQ ID NO: 12.

57. A host cell comprising the vector of claim 56.

58. A method of making a recombinant host cell integrant comprising:
introducing into said host cell a vector comprising the polynucleotide sequence of pLOI2306 (SEQ ID NO: 12); and
identifying a host cell having said vector stably integrated.

59. A method for expressing a polysaccharase in a host cell comprising:
introducing into said host cell a vector comprising the polynucleotide sequence of pLOI2306 (SEQ ID NO: 12); and
identifying a host cell expressing said polysaccharase.

60. The method of claim 58 wherein said host cell is ethanologenic.

61. A method for producing ethanol from an oligosaccharide source comprising,
contacting said oligosaccharide source with a recombinant ethanologenic host cell according to claim 18, 19 or 31,
wherein expression of said first and second polynucleotide segments results in the increased production of polysaccharase activity by the ethanologenic cell such that the oligosaccharide source is enzymatically degraded and fermented into ethanol.

62. The method of claim 61 wherein said polysaccharase is selected from the group consisting of glucanase, endoglucanase, exoglucanase, cellobiohydrolase, α-glucosidase, endo-1,4-α-xylanase, β-xylosidase, β-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

63. The method of claim 62 wherein said polysaccharase is glucanase.

64. The method according to claim 63 wherein said glucanase is an expression product of a celZ gene.

65. The method of claim 64 wherein said celZ gene is derived from *Erwinia chrysanthemi*.

66. The method of claim 61 wherein said second heterologous polynucleotide segment comprises at least one pul gene or out gene.

67. The method of claim 61 wherein said host cell is selected from the family Enterobacteriaceae.

68. The method of claim 61 wherein said host cell is selected from the group consisting of *Escherichia* and *Klebsiella*.

69. The method of claim 61, wherein said host cell is selected from the group consisting of *E. coli* KO4 (ATCC 55123), *E. coli* KO11 (ATCC 55124), *E. coli* KO12 (ATCC 55125), *K. oxytoca* M5A1, and *K. oxytoca* P2 (ATCC 55307).

70. The method of claim 61, wherein said method is conducted in an aqueous solution.

71. The method of claim 61, wherein said oligosaccharide is selected from the group consisting of lignocellulose, hemicellulose, cellulose, pectin, and any combination thereof.

72. The method according to claim 61, wherein said first heterologous polynucleotide segment is, or derived from, pLOI2306 (SEQ ID NO: 12).

73. The recombinant host cell of claim 2, wherein said second heterologous polynucleotide comprises *Erwinia* out genes.

74. The recombinant host cell of claim 18, wherein said recombinant host cell comprises heterologous adh and pdc genes.

* * * * *

SEQUENCE LISTING

```
<160> NUMBER OF SEQ ID NOS: 12

<210> SEQ ID NO 1
<211> LENGTH: 450
<212> TYPE: DNA
<213> ORGANISM: Zymomonas mobilis
<220> FEATURE:
<223> OTHER INFORMATION: promoter

<400> SEQUENCE: 1 cttttt cggc atgagcaacc aacattttca aggtatcatc ctgatgcgca atatcggcat     60
cggttagcca taaccatttt acctgtccgg cggccttaat accttgatca gatggttcgt    120
ggtgttgtta ccttgccgaa gggcaccggt aaaaatgttc gcgtcggtgt tttcgcccgt    180
ggcccgaaag ctgaagaagc taaagctgct ggtgcagaag ttgtcggcgc agaagacctg    240
atggaagcca ttcagggcgg cagcattgat ttcgatcgtg atgccctta tactgaaatt     300 gccttgcgct gccataatga agcagcctcc ggtgttttgg cagatttaag cgctgcctga    360
ttttcgtgat cctctagagt ctatgaaatg gagattcatt tatgcctctc tcttattcgg    420
ataaccatcc agtcatccgc aagcttggcc                                     450

<210> SEQ ID NO 2
<211> LENGTH: 1509
<212> TYPE: DNA
<213> ORGANISM: Zymomonas mobilis
<220> FEATURE:
<223> OTHER INFORMATION: expression
      vector

<400> SEQUENCE: 2
gatcaaccgg caatttatcc acggcatcaa attcgatctg tcttttcccg tatcattggc     60
aataccggca ttctgattac aggccgtgtt ttgaatgcgg tatgcagttt tgtctatgtc    120
gcatggacat cccagacatt gggattgaac ctgtttggtg tcatgctttt gattacgact    180
tttgctaccc tgatttcgga tattacccgt tttcagtcat ggcaaacctt gctgcattac    240
ggttcaaaag cttttcagga aaagatttt aaccaatttg atgatgtcct tgccttttgc    300
atcagagccg atttttttag tgcggcgata ggtatgttgg tagggttagg cggtatcttg    360
attttaggca cttcaagatt gggatggcct gccgaggtca agccagatgc cttgcttgt     420 atgctgatta tactttttat gaatatcggc tggtccaacc gggatgttgc ggctgtgtaa    480
ccgctttaaa ctggtcacta tttatgagtt tattacgacc tgcgtcagaa ccggaggttg    540
tggcattggt tattggcttc atatgccttt ggggtatttt ttgtttatat ggtgcctgac    600
gcaattcacg cttttgtca cctgtagtta cgctggcatt tatctctttc accaatatac    660
ggagcgagca tttccgataa gaaaaatatt tcagagaaaa acgcccgttg aagggatgtg    720
gaaattcact ttaagcgtca gttttaatga aatcctagac tccatttcc agcagggtgg     780 caccctgct attggtagct cactgggggc tggggaagcg gctgtctatc gggtcgcgcg    840
ccagattagt aacggtttat ccaaaccagc acagatgatg atcggctaac atgcatccac    900
cggcagcacc ggccgtttta tgcttgggat tattgatatg ccgaaaagga tacaacatct    960
ggaagaaaaa gacgaaggcc ggaataagcg cccattctgc aaaattgtta caacttagtc   1020
```

```
gcgccatcag ggaatgaaaa atcaatccgt cttttcggc atgagcaacc aacatttca      1080 aggtatcatc ctgatgcgca atatcggcat cggttagcca taaccatttt acctgtccgg     1140
cggccttaat accttgatca gatggttcgt ggtgttgtta ccttgccgaa gggcaccggt     1200
aaaaatgttc gcgtcggtgt tttcgcccgt ggcccgaaag ctgaagaagc taaagctgct     1260
ggtgcagaag ttgtcggcgc agaagacctg atggaagcca ttcagggcgg cagcattgat     1320
ttcgatcgtg atgcccttta tactgaaatt gccttgcgct gccataatga agcagcctcc     1380
ggtgttttgg cagatttaag cgctgcctga ttttcgtgat cctctagagt ctatgaaatg     1440
gagattcatt tatgcctctc tcttattcgg ataaccatcc agtcatccgc aagcttggcc     1500
gtaatccat                                                              1509
```

<210> SEQ ID NO 3
<211> LENGTH: 27
<212> TYPE: DNA
<213> ORGANISM: Escherichia coli
<220> FEATURE:
<223> OTHER INFORMATION: Description of Artificial Sequence:primer

<400> SEQUENCE: 3
cgaattcctg ccgaagttta ttagcca                                          27

<210> SEQ ID NO 4
<211> LENGTH: 31
<212> TYPE: DNA
<213> ORGANISM: Escherichia coli
<220> FEATURE:
<223> OTHER INFORMATION: Description of Artificial Sequence:primer

<400> SEQUENCE: 4
aaggatcctt ccaccagcta tttgttagtg a                                     31

<210> SEQ ID NO 5
<211> LENGTH: 27
<212> TYPE: DNA
<213> ORGANISM: Escherichia coli
<220> FEATURE:
<223> OTHER INFORMATION: Description of Artificial Sequence:primer

<400> SEQUENCE: 5
agaattctgc cagttggttg acgatag                                          27

<210> SEQ ID NO 6
<211> LENGTH: 30
<212> TYPE: DNA
<213> ORGANISM: Escherichia coli
<220> FEATURE:
<223> OTHER INFORMATION: Description of Artificial Sequence:primer

<400> SEQUENCE: 6
caggatcccc tcaagtcact agttaaactg                                       30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 7
taatacgact cactataggg                                                  20

```
<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 8
taacaatttc acacagga                                              18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 9
cacgacgttg taaaacgac                                             19

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 10
gactggatgg ttatccgaat aagagagagg                                 30

<210> SEQ ID NO 11
<211> LENGTH: 8
<212> TYPE: DNA
<213> ORGANISM: Artificial Sequence
<220> FEATURE:
<223> OTHER INFORMATION: Description of Artificial Sequence:primer

<400> SEQUENCE: 11 ggcgcgcc                                                          8

<210> SEQ ID NO 12
<211> LENGTH: 11544
<212> TYPE: DNA
<213> ORGANISM: Artificial Sequence
<220> FEATURE:
<223> OTHER INFORMATION: Description of Artificial Sequence:vector
<223> OTHER INFORMATION: all occurrences of n to be sequenced
<223> OTHER INFORMATION: nucleotide positions 1-1451 ecodes promoter
<223> OTHER INFORMATION: nucleotide positions 1452-2735 encodes celZ
      gene
<223> OTHER INFORMATION: nucleotide positions 4916-5776 encodes bla gene
<223> OTHER INFORMATION: nucleotide positions 7061-8251 encodes tet gene
<220> FEATURE:
<221> NAME/KEY: CDS
<222> LOCATION: (1452)..(2735)
<223> OTHER INFORMATION: nucleotide positions 9476-11544 encodes target
      sequence from K. oxytoca
<220> FEATURE:
<221> NAME/KEY: CDS
<222> LOCATION: (4916)..(5776)
<220> FEATURE:
<221> NAME/KEY: CDS
<222> LOCATION: (7061)..(8251)

<400> SEQUENCE: 12
gatcaaccgg caatttatcc acggcatcaa attcgatctg tcttttcccg tatcattggc    60
aataccggca ttctgattac aggccgtgtt ttgaatgcgg tatgcagttt tgtctatgtc   120
gcatggacat cccagacatt gggattgaac ctgtttggtg tcatgctttt gattacgact   180
```

```
tttgctaccc tgatttcgga tattacccgt tttcagtcat ggcaaacctt gctgcattac      240
ggttcaaaag cttttcagga aaaagatttt aaccaatttg atgatgtcct tgccttttgc      300
atcagagccg atttttttag tgcggcgata ggtatgttgg tagggttagg cggtatcttg      360
attttaggca cttcaagatt gggatggcct gccgaggtca agccagatgc cttgctttgt      420
atgctgatta tacttttat gaatatcggc tggtccaacc gggatgttgc ggctgtgtaa       480
ccgctttaaa ctggtcacta tttatgagtt tattacgacc tgcgtcagaa ccggaggttg      540
tggcattggt tattggcttc atatgccttt ggggtatttt ttgtttatat ggtgcctgac      600
gcaattcacg cttttgtca cctgtagtta cgctggcatt tatctctttc accaatatac       660
ggagcgagca tttccgataa gaaaaatatt tcagagaaaa acgcccgttg aagggatgtg      720
gaaattcact ttaagcgtca gttttaatga atcctagac tccattttcc agcagggtgg       780 caccccttgct attggtagct cactgggggc tggggaagcc gctgtctatc gggtcgcgcg     840
ccagattagt aacggtttat ccaaaccagc acagatgatg atcggctaac atgcatccac      900
cggcagcacc ggccgtttta tgcttgggat tattgatatg ccgaaaagga tacaacatct      960
ggaagaaaaa gacgaaggcc ggaataagcg cccattctgc aaaattgtta caacttagtc     1020
gcgccatcag ggaatgaaaa atcaatccgt cttttcggc atgagcaacc aacatttttca    1080 aggtatcatc ctgatgcgca atatcggcat cggttagcca taaccatttt acctgtccgg     1140 cggcctaat accttgatca gatggttcgt ggtgttgtta ccttgccgaa gggcaccggt      1200
aaaaatgttc gcgtcggtgt tttcgcccgt ggcccgaaag ctgaagaagc taaagctgct     1260
ggtgcagaag ttgtcggcgc agaagacctg atggaagcca ttcagggcgg cagcattgat     1320
ttcgatcgtg atgcccttta tactgaaatt gccttgcgct gccataatga agcagcctcc     1380
ggtgttttgg cagatttaag cgctgcctga ttttcgtgat cctctagagt ctatgaaatg     1440
gagattcatt t atg cct ctc tct tat tcg gat aac cat cca gtc atc gat     1490
              Met Pro Leu Ser Tyr Ser Asp Asn His Pro Val Ile Asp
              1               5                  10 agc caa aaa cac gcc cca cgt aaa aaa ctg ttt cta tct tgt gcc tgt       1538
Ser Gln Lys His Ala Pro Arg Lys Lys Leu Phe Leu Ser Cys Ala Cys
 15                  20                  25 tta gga tta agc ctt gcc tgc ctt tcc agt aat gcc tgg gcg agt gtt       1586
Leu Gly Leu Ser Leu Ala Cys Leu Ser Ser Asn Ala Trp Ala Ser Val
 30                  35                  40                  45 gag ccg tta tcc gtt agc ggc aat aaa atc tac gca ggt gaa aaa gcc       1634
Glu Pro Leu Ser Val Ser Gly Asn Lys Ile Tyr Ala Gly Glu Lys Ala
              50                  55                  60 aaa agt ttt gcc ggc aac agc tta ttc tgg agt aat aat ggt tgg ggt       1682
Lys Ser Phe Ala Gly Asn Ser Leu Phe Trp Ser Asn Asn Gly Trp Gly
          65                  70                  75 ggg gaa aaa ttc tac aca gcc gat acc gtt gcg tcg ctg aaa aaa gac       1730
Gly Glu Lys Phe Tyr Thr Ala Asp Thr Val Ala Ser Leu Lys Lys Asp
 80                  85                  90 tgg aaa tcc agc att gtt cgc gcc gct atg ggc gtt cag gaa agc ggt       1778
Trp Lys Ser Ser Ile Val Arg Ala Ala Met Gly Val Gln Glu Ser Gly
 95                  100                 105 ggt tat ctg cag gac ccg gct ggc aac aag gcc aaa gtt gaa aga gtg       1826
Gly Tyr Leu Gln Asp Pro Ala Gly Asn Lys Ala Lys Val Glu Arg Val
110                 115                 120                 125 gtg gat gcc gca atc gcc aac gat atg tat gtg att att gac tgg cac       1874
Val Asp Ala Ala Ile Ala Asn Asp Met Tyr Val Ile Ile Asp Trp His
              130                 135                 140
```

```
                                         -continued tca cat tct gca gaa aac aat cgc agt gaa gcc att cgc ttc ttc cag         1922
Ser His Ser Ala Glu Asn Asn Arg Ser Glu Ala Ile Arg Phe Phe Gln
            145                 150                 155 gaa atg gcg cgc aaa tat ggc aac aag ccg aat gtc att tat gaa atc         1970
Glu Met Ala Arg Lys Tyr Gly Asn Lys Pro Asn Val Ile Tyr Glu Ile
        160                 165                 170 tac aac gag ccg ctt cag gtt tca tgg agc aat acc att aaa cct tat         2018
Tyr Asn Glu Pro Leu Gln Val Ser Trp Ser Asn Thr Ile Lys Pro Tyr
175                 180                 185 gcc gaa gcc gtg att tcc gcc att cgc gcc att gac ccg gat aac ctg         2066
Ala Glu Ala Val Ile Ser Ala Ile Arg Ala Ile Asp Pro Asp Asn Leu
190                 195                 200                 205 att att gtc ggt acg ccc agt tgg tcg caa aac gtt gat gaa gcg tcg         2114
Ile Ile Val Gly Thr Pro Ser Trp Ser Gln Asn Val Asp Glu Ala Ser
                210                 215                 220 cgc gat cca atc aac gcc aag aat atc gcc tat acg ctg cat ttc tac         2162
Arg Asp Pro Ile Asn Ala Lys Asn Ile Ala Tyr Thr Leu His Phe Tyr
            225                 230                 235 gcg gga acc cat ggt gag tca tta cgc act aaa gcc cgc cag gcg tta         2210
Ala Gly Thr His Gly Glu Ser Leu Arg Thr Lys Ala Arg Gln Ala Leu
        240                 245                 250 aat aac ggt att gcg ctt ttc gtc acc gag tgg ggc gcc gtt aac gcg         2258
Asn Asn Gly Ile Ala Leu Phe Val Thr Glu Trp Gly Ala Val Asn Ala
    255                 260                 265 gac ggc aat ggc gga gtg aac cag aca gat acc gac gcc tgg gta acg         2306
Asp Gly Asn Gly Gly Val Asn Gln Thr Asp Thr Asp Ala Trp Val Thr
270                 275                 280                 285 ttc atg cgt gac aac aac atc agc aac gca aac tgg gcg tta aat gat         2354
Phe Met Arg Asp Asn Asn Ile Ser Asn Ala Asn Trp Ala Leu Asn Asp
                290                 295                 300 aaa agc gaa ggg gca tca acc tat tat ccg gac tct aaa aac ctg acc         2402
Lys Ser Glu Gly Ala Ser Thr Tyr Tyr Pro Asp Ser Lys Asn Leu Thr
            305                 310                 315 gag tcg ggt aaa ata gta aaa tcg atc att caa agc tgg cca tat aaa         2450
Glu Ser Gly Lys Ile Val Lys Ser Ile Ile Gln Ser Trp Pro Tyr Lys
        320                 325                 330 gcg ggc agc gcc gcc agt aca aca acc gat cag tca acc gat acc acc         2498
Ala Gly Ser Ala Ala Ser Thr Thr Thr Asp Gln Ser Thr Asp Thr Thr
    335                 340                 345 atg gca cca ccg ttg acg aac cga cca caa ccg aca cac cgg caa acc         2546
Met Ala Pro Pro Leu Thr Asn Arg Pro Gln Pro Thr His Arg Gln Thr
350                 355                 360                 365 gct gat tgc tgc aat gcc aac gtt tac ccc aac tgg gtt agc aaa gac         2594
Ala Asp Cys Cys Asn Ala Asn Val Tyr Pro Asn Trp Val Ser Lys Asp
                370                 375                 380 tgg gcg ggc cgg cag cga ctc ata acg aag cag gcc aat cga tcg tct         2642
Trp Ala Gly Arg Gln Arg Leu Ile Thr Lys Gln Ala Asn Arg Ser Ser
            385                 390                 395 aca aag gga acc tgt ata ccg caa act ggt aca ctt cat ccg ttc cgg         2690
Thr Lys Gly Thr Cys Ile Pro Gln Thr Gly Thr Leu His Pro Phe Arg
        400                 405                 410 gca gcg att cct cct ggg cac agg ttg gta gct gta act aat tga             2735
Ala Ala Ile Pro Pro Gly His Arg Leu Val Ala Val Thr Asn
    415                 420                 425 ttaatctttt cacccccaaa ataacagggc tgcgattgca gcctgatacg caacattcca       2795
ttacttaatt gcgttcaaaa gcgcccaaat ccggtgcgct gccttgtaac taatatgatt       2855
tctctttcgt acccgcgtta atcagctttg agttagccga cagacggaac agcgaggttg       2915
ccggcaacgt gccgtcatta tcacgagata cggtagccag cgaggtgtcc aggctgacga       2975
```

```
atcggacgcg gaagccgctg tccgtatcca tgagttgact cgcatccgca ttactgaccg    3035
ttgcagaagc agacagagac acgttgttgc ggaagtaatg tttctgtcct gactggacgt    3095
tgctcccgaa agcataatta atgccgtttt tatatgacgt gttatttatt accgtacgcc    3155
gccgcgttat tgttctggtc aaaacctttg ctcacgttgc caaacgcgac gcaacgggta    3215
atgcgatgat tgccgaccgc tggttcctcc cagtttgaac ccgttggcat tgccggcgaa    3275
cgcgctnnnn nnnnnnnnnn nnnnnnnnnn nnnnnnnnnn nnnnnnnnnn nnnnnnnnnn    3335
nnnnnnnnnn nnnnnnnnnn nnnnnnnnnn nnnnnnnnnn nnnnnnnnnn nnnnnnnnnn    3395
nnnnnnnnnn nnnnnnnnnn nnnnnnnnnn nnnnnnnnnn nnnnnnnnnn nnnnnnnnnn    3455
nnnnnnnnnn nnnnnnnnnn nnnnnnnnnn nnnnnnnnnn nnnnnnnnnn nnnnnnnnnn    3515
nnnnnnnnnn nnnnnnnnnn nnnnnnnnnn nnnnnnnnnn nnnnnnnnnn nnnnnnnnnn    3575
nnnnnnnnnn nnnnnnnnnn nnnnnnnnnn nnnnnnnnnn nnnnnnnnnn nnnnnnnnnn    3635
nnnnnnnnnn nnnnnnnnnn nnnnnnnnnn nnnnnnnnnn nnnnnnnnnn nnnnnnnnnn    3695
nnnnnnnnnn nnnnnnnnnn nnnnnnnnnn nnnnnnnnnn nnnnnnnnnn nnnnnnnnnn    3755
nnnnnnnnnn nnnnnnnnnn nnnnnnnnnn nnnnnnnnnn nnnnnnnnnn nnnnnnnnnn    3815
nnnnnnnnnn nnnnnnnnnn nnnnnnnnnn nnnnnnnnnn nnnnnnnnnn nnnnnnnnnn    3875
nnnnnnnnnn nnnnnnnnnn nnnnnnnnnn nnnnnnnnnn nnnnnnnnnn nnnnnnnnnn    3935
nnnnnnnnnn nnnnnnnnnn nnnnnnnnnn nnnnnnnnnn nnnnnnnnnn nnnnnnnnnn    3995
nnnnnnnnnn nnnnnnnnnn nnnnnnnnnn nnnnnnnnnn nnnnnnnnnn nnnnnnnnnn    4055
nnnnnnnnnn nnnnnnnnnn nnnnnnnnnn nnnnnnnnnn nnnnnnnnnn nnnnnnnnnn    4115
nnnnnnnnnn nnnnnnnnnn nnnnnnnnnn nnnnnnnnnn nnnnnnnnnn nnnnnnnnnn    4175
nnnnnnnnnn nnnnnnnnnn nnnnnnnnnn nnnnnnnnnn nnnnnnnnnn nnnnnnnnnn    4235
nnnnnnnnnn nnnnnnnnnn nnnnnnnnnn nnnnnnnnnn nnnnnngatc ctctagagtc    4295
gacctgcagg aattcactgg ccgtcgtttt acaacgtcgt gactgggaaa accctggcgt    4355
tacccaactt aatcgccttg cagcacatcc ccctttcgcc agctggcgta atagcgaaga    4415
ggcccgcacc gatcgccctt cccaacagtt gcgcagcctg aatggcgaat ggcgcctgat    4475 gcggtattt tccttacgc atctgtgcgg tatttcacac cgcataggcg cgcctatggt    4535
gcactctcag tacaatctgc tctgatgccg catagttaag ccagccccga cacccgccaa    4595
cacccgctga cgcgccctga cgggcttgtc tgctcccggc atccgcttac agacaagctg    4655
tgaccgtctc cgggagctgc atgtgtcaga ggttttcacc gtcatcaccg aaacgcgcga    4715
gacgaaaggg cctcgtgata cgcctatttt tataggttaa tgtcatgata taatggtttt    4775
cttagacgtc aggtggcact tttcggggaa atgtgcgcgg aacccctatt tgtttatttt    4835
tctaaataca ttcaaatatg tatccgctca tgagacaata accctgataa atgcttcaat    4895
aatattgaaa aaggaagagt atg agt att caa cat ttc cgt gtc gcc ctt att    4948
                     Met Ser Ile Gln His Phe Arg Val Ala Leu Ile
                      1               5                  10 ccc ttt ttt gcg gca ttt tgc ctt cct gtt ttt gct cac cca gaa acg    4996
Pro Phe Phe Ala Ala Phe Cys Leu Pro Val Phe Ala His Pro Glu Thr
                15                  20 ctg gtg aaa gta aaa gat gct gaa gat cag ttg ggt gca cga gtg ggt    5044
Leu Val Lys Val Lys Asp Ala Glu Asp Gln Leu Gly Ala Arg Val Gly
        30                  35                  40 tac atc gaa ctg gat ctc aac agc ggt aag atc ctt gag agt ttt cgc    5092
Tyr Ile Glu Leu Asp Leu Asn Ser Gly Lys Ile Leu Glu Ser Phe Arg
```

```
                                                         -continued
              50
ccc gaa gaa cgt ttt cca atg atg agc act ttt aaa gtt ctg cta tgt    5140
Pro Glu Glu Arg Phe Pro Met Met Ser Thr Phe Lys Val Leu Leu Cys
 60                                      70 ggc gcg gta tta tcc cgt att gac gcc ggg caa gag caa ctc ggt cgc    5188
Gly Ala Val Leu Ser Arg Ile Asp Ala Gly Gln Glu Gln Leu Gly Arg
             80                                      90 cgc ata cac tat tct cag aat gac ttg gtt gag tac tca cca gtc aca    5236
Arg Ile His Tyr Ser Gln Asn Asp Leu Val Glu Tyr Ser Pro Val Thr
                          100 gaa aag cat ctt acg gat ggc atg aca gta aga gaa tta tgc agt gct    5284
Glu Lys His Leu Thr Asp Gly Met Thr Val Arg Glu Leu Cys Ser Ala
         110                                     120 gcc ata acc atg agt gat aac act gcg gcc aac tta ctt ctg aca acg    5332
Ala Ile Thr Met Ser Asp Asn Thr Ala Ala Asn Leu Leu Leu Thr Thr
                     130 atc gga gga ccg aag gag cta acc gct ttt ttg cac aac atg ggg gat    5380
Ile Gly Gly Pro Lys Glu Leu Thr Ala Phe Leu His Asn Met Gly Asp
140                                     150 cat gta act cgc ctt gat cgt tgg gaa ccg gag ctg aat gaa gcc ata    5428
His Val Thr Arg Leu Asp Arg Trp Glu Pro Glu Leu Asn Glu Ala Ile
             160                                     170 cca aac gac gag cgt gac acc acg atg cct gta gca atg gca aca acg    5476
Pro Asn Asp Glu Arg Asp Thr Thr Met Pro Val Ala Met Ala Thr Thr
                          180 ttg cgc aaa cta tta act ggc gaa cta ctt act cta gct tcc cgg caa    5524
Leu Arg Lys Leu Leu Thr Gly Glu Leu Leu Thr Leu Ala Ser Arg Gln
         190                                     100 caa tta ata gac tgg atg gag gcg gat aaa gtt gca gga cca ctt ctg    5572
Gln Leu Ile Asp Trp Met Glu Ala Asp Lys Val Ala Gly Pro Leu Leu
                     110 cgc tcg gcc ctt ccg gct ggc tgg ttt att gct gat aaa tct gga gcc    5620
Arg Ser Ala Leu Pro Ala Gly Trp Phe Ile Ala Asp Lys Ser Gly Ala
120                                     130 ggt gag cgt ggg tct cgc ggt atc att gca gca ctg ggg cca gat ggt    5668
Gly Glu Arg Gly Ser Arg Gly Ile Ile Ala Ala Leu Gly Pro Asp Gly
             140                                     150 aag ccc tcc cgt atc gta gtt atc tac acg acg ggg agt cag gca act    5716
Lys Pro Ser Arg Ile Val Val Ile Tyr Thr Thr Gly Ser Gln Ala Thr
                          160 atg gat gaa cga aat aga cag atc gct gag ata ggt gcc tca ctg att    5764
Met Asp Glu Arg Asn Arg Gln Ile Ala Glu Ile Gly Ala Ser Leu Ile
         170                                     180 aag cat tgg taa ctgtcagacc aagtttactc atatatactt tagattgatt        5816
Lys His Trp
         185 taaaacttca tttttaattt aaaaggatct aggtgaagat cctttttgat aatctcatga  5876 ccaaaatccc ttaacgtgag ttttcgttcc actgagcgtc agaccccgta gaaaagatca  5936 aaggatcttc ttgagatcct ttttttctgc gcgtaatctg ctgcttgcaa acaaaaaaac  5996 caccgctacc agcggtggtt tgtttgccgg atcaagagct accaactctt tttccgaagg  6056 taactggctt cagcagagcg cagataccaa atactgtcct tctagtgtag ccgtagttag  6116 gccaccactt caagaactct gtagcaccgc ctacatacct cgctctgcta atcctgttac  6176 cagtggctgc tgccagtggc gataagtcgt gtcttaccgg gttggactca agacgatagt  6236 taccggataa ggcgcagcgg tcgggctgaa cggggggttc gtgcacacag cccagcttgg  6296 agcgaacgac ctacaccgaa ctgagatacc tacagcgtga gctatgagaa agcgccacgc  6356
```

-continued

```
ttcccgaagg gagaaaggcg gacaggtatc cggtaagcgg cagggtcgga acaggagagc    6416
gcacgaggga gcttccaggg ggaaacgcct ggtatcttta tagtcctgtc gggtttcgcc    6476
acctctgact tgagcgtcga ttttgtgat gctcgtcagg ggggcggagc ctatggaaaa     6536
acgccagcaa cgcggccttt tacggttcc tggccttttg ctggcctttt gctcacatgt     6596
tctttcctgc gttatcccct gattctgtgg ataaccgtat taccgccttt gagtgagctg    6656
ataccgctcg ccgcagccga acgaccgagc gcagcgagtc agtgagcgag gaagcggcgc    6716
gccagcggaa gagcgcccaa tacgcaaacc gcctctcccc gcgcgttggc cgattcatta    6776
atgcagctgg cacgacaggt ttcccgactg gaaagcgggc agtgagcgca acgcaattaa    6836
tgtgagttag ctcactcatt aggcacccca ggctttacac tttatgcttc cggctcgtat    6896
gttgtgtgga attgtgagcg gataacaatt tcacacagga aacagctatg accatgatta    6956
cgccaagctt gcatgccaat tctcatgttt gacagcttat catcgataag ctttaatgcg    7016
gtagtttatc acagttaaat tgctaacgca gtcaggcacc gtgt atg aaa tct aac     7072
                                              Met Lys Ser Asn
                                                1
```

| aat gcg ctc atc gtc atc ctg ggc acc gtc acc ctg gat gct gta ggc | 7120 |
|---|---|
| Asn Ala Leu Ile Val Ile Leu Gly Thr Val Thr Leu Asp Ala Val Gly | |
|              10                            20 | |

```
ata ggc ttg gtt atg ccg gta ctg ccg ggc ctc ttg cgg gat atc gtc    7168
Ile Gly Leu Val Met Pro Val Leu Pro Gly Leu Leu Arg Asp Ile Val
                            30 cat tcc gac agc atc gcc agt cac tat ggc gtg ctg cta gcg cta tat    7216
His Ser Asp Ser Ile Ala Ser His Tyr Gly Val Leu Leu Ala Leu Tyr
             40                              50 gcg ttg atg caa ttt cta tgc gca ccc gtt ctc gga gca ctg tcc gac    7264
Ala Leu Met Gln Phe Leu Cys Ala Pro Val Leu Gly Ala Leu Ser Asp
                         60 cgc ttt ggc cgc cgc cca gtc ctg ctc gct tcg cta ctt gga gcc act    7312
Arg Phe Gly Arg Arg Pro Val Leu Leu Ala Ser Leu Leu Gly Ala Thr
         70                              80 atc gac tac gcg atc atg gcg acc aca ccc gtc ctg tgg atc ctc tac    7360
Ile Asp Tyr Ala Ile Met Ala Thr Thr Pro Val Leu Trp Ile Leu Tyr
                     90                             100 gcc gga cgc atc gtg gcc ggc atc acc ggc gcc aca ggt gcg gtt gct    7408
Ala Gly Arg Ile Val Ala Gly Ile Thr Gly Ala Thr Gly Ala Val Ala
                                110 ggc gcc tat atc gcc gac atc acc gat ggg gaa gat cgg gct cgc cac    7456
Gly Ala Tyr Ile Ala Asp Ile Thr Asp Gly Glu Asp Arg Ala Arg His
             120                             130 ttc ggg ctc atg agc gct tgt ttc ggc gtg ggt atg gtg gca ggc ccc    7504
Phe Gly Leu Met Ser Ala Cys Phe Gly Val Gly Met Val Ala Gly Pro
                        140 gtg gcc ggg gga ctg ttg ggc gcc atc tcc ttg cat gca cca ttc ctt    7552
Val Ala Gly Gly Leu Leu Gly Ala Ile Ser Leu His Ala Pro Phe Leu
    150                             160 gcg gcg gcg gtg ctc aac ggc ctc aac cta cta ctg ggc tgc ttc cta    7600
Ala Ala Ala Val Leu Asn Gly Leu Asn Leu Leu Leu Gly Cys Phe Leu
                 170                             180 atg cag gag tcg cat aag gga gag cgt cga ccg atg ccc ttg aga gcc    7648
Met Gln Glu Ser His Lys Gly Glu Arg Arg Pro Met Pro Leu Arg Ala
                            190 ttc aac cca gtc agc tcc ttc cgg tgg gcg cgg ggc atg act atc gtc    7696
Phe Asn Pro Val Ser Ser Phe Arg Trp Ala Arg Gly Met Thr Ile Val
        200                             210 gcc gca ctt atg act gtc ttc ttt atc atg caa ctc gta gga cag gtg    7744
```

```
                                              -continued

Ala Ala Leu Met Thr Val Phe Phe Ile Met Gln Leu Val Gly Gln Val
                            220 ccg gca gcg ctc tgg gtc att ttc ggc gag gac cgc ttt cgc tgg agc    7792
Pro Ala Ala Leu Trp Val Ile Phe Gly Glu Asp Arg Phe Arg Trp Ser
    230                                 240 gcg acg atg atc ggc ctg tcg ctt gcg gta ttc gga atc ttg cac gcc    7840
Ala Thr Met Ile Gly Leu Ser Leu Ala Val Phe Gly Ile Leu His Ala
                    250                                 260 ctc gct caa gcc ttc gtc act ggt ccc gcc acc aaa cgt ttc ggc gag    7888
Leu Ala Gln Ala Phe Val Thr Gly Pro Ala Thr Lys Arg Phe Gly Glu
                                        270 aag cag gcc att atc gcc ggc atg gcg gcc gac gcg ctg ggc tac gtc    7936
Lys Gln Ala Ile Ile Ala Gly Met Ala Ala Asp Ala Leu Gly Tyr Val
            180                                 190 ttg ctg gcg ttc gcg acg cga ggc tgg atg gcc ttc ccc att atg att    7984
Leu Leu Ala Phe Ala Thr Arg Gly Trp Met Ala Phe Pro Ile Met Ile
                        200 ctt ctc gct tcc ggc ggc atc ggg atg ccc gcg ttg cag gcc atg ctg    8032
Leu Leu Ala Ser Gly Gly Ile Gly Met Pro Ala Leu Gln Ala Met Leu
    210                                 220 tcc agg cag gta gat gac gac cat cag gga cag ctt caa gga tcg ctc    8080
Ser Arg Gln Val Asp Asp Asp His Gln Gly Gln Leu Gln Gly Ser Leu
                    230                                 240 gcg gct ctt acc agc cta act tcg atc act gga ccg ctg atc gtc acg    8128
Ala Ala Leu Thr Ser Leu Thr Ser Ile Thr Gly Pro Leu Ile Val Thr
                                250 gcg att tat gcc gcc tcg gcg agc aca tgg aac ggg ttg gca tgg att    8176
Ala Ile Tyr Ala Ala Ser Ala Ser Thr Trp Asn Gly Leu Ala Trp Ile
            260                                 270 gta ggc gcc gcc cta tac ctt gtc tgc ctc ccc gcg ttg cgt cgc ggt    8224
Val Gly Ala Ala Leu Tyr Leu Val Cys Leu Pro Ala Leu Arg Arg Gly
                        280 gca tgg agc cgg gcc acc tcg acc tga atggaagccg gcggcacctc          8271
Ala Trp Ser Arg Ala Thr Ser Thr
    290 gctaacggat tcaccactcc aagaattgga gccaatcaat tcttgcggag aactgtgaat  8331
gcgcaaacca acccttggca gaacatatcc atcgcgtccg ccatctccag cagccgcacg  8391
cggcgcatct cggggtcgac tctagaggat ccccgcaacg ctgtcagcgc tttccagtta  8451
aacggctcca acgtcgccat aggtaattcc tcgcccggcc atacgatcgg gcaggtgccg  8511
ttggctatcg ccgtcgcctg actcatcaca ctatcttccg ctgcatcgcg aagggttttg  8571
accacttctt ccatctctcc gtgcgccgga tgccatgctc acgtacgcgg cttatcagat  8631
agtcgggcag gccgtcgttc cagcccaatg aggggaagct ggcgtggagc gatgccagca  8691
cctgctcctc aacaccgtaa tggccggcgg cgaacaggca ttcggcggta agcgcttcca  8751
gcccttttaat catcacgctg cggcacatct tgatagccga cacgctgcca acgtggttac  8811
caccatagcg ggcgttacat ccaagcgtgg tgagtaattc agcaattgcc tctgcctgtg  8871
gtcccccgt caacagcggc gttcggagtg cccctggggg gaccggcgcc atcaccgcta   8931
catcgacata agcgccgggc ttaaagcatt tggcagcctg acgcttggtc tgcggggcga  8991
cggagttaag gtcaagaaaa tactgcgtgt cggtcatcag cggtgcagct tgtgaggcga  9051
catccagggc ggatcccgcg gtgacggtgg aaaatatgag ttcggcacct gtcaacgcgt  9111
cagccaggga gattgccgcc cgcacgcctc cccgatgcgc cttcgttatc atcgcatcgc  9171
gctcaggacc ttgcagcttg caatcccaga cggtgactgg gttcacttt  gccagtgcat  9231
```

```
ccgcaagaat gccacctgct tcaccataac ctataaacgt tattgtcgtc ataacagctc     9291
cttacgcggc cacacgtcgg ccggaatgca aacgtcgccc gcgaacagaa gtcgcgccgt     9351
acgcagcaga ccgcagcctg ccaactgccc attatcatca agccggagcg ccacgctgaa     9411
ttgggtaccg agctccgaat tgggtaccga gctcgaatta attcgagctc ggtacccggg     9471
gatcnnnnnn nnnnnnnnnn nnnnnnnnnn nnnnnnnnnn nnnnnnnnnn nnnnnnnnnn     9531
nnnnnnnnnn nnnnnnnnnn nnnnnnnnnn nnnnnnnnnn nnnnnnnnnn nnnnnnnnnn     9591
nnnnnnnnnn nnnnnnnnnn nnnnnnnnnn nnnnnnnnnn nnnnnnnnnn nnnnnnnnnn     9651
nnnnnnnnnn nnnnnnnnnn nnnnnnnnnn nnnnnnnnnn nnnnnnnnnn nnnnnnnnnn     9711
nnnnnnnnnn nnnnnnnnnn nnnnnnnnnn nnnnnnnnnn nnnnnnnnnn nnnnnnnnnn     9771
nnnnnnnnnn nnnnnnnnnn nnnnnnnnnn nnnnnnnnnn nnnnnnnnnn nnnnnnnnnn     9831
nnnnnnnnnn nnnnnnnnnn nnnnnnnnnn nnnnnnnnnn nnnnnnnnnn nnnnnnnnnn     9891
nnnnnnnnnn nnnnnnnnnn nnnnnnnnnn nnnnnnnnnn nnnnnnnnnn nnnnnnnnnn     9951
nnnnnnnnnn nnnnnnnnnn nnnnnnnnnn nnnnnnnnnn nnnnnnnnnn nnnnnnnnnn    10011
nnnnnnnnnn nnnnnnnnnn nnnnnnnnnn nnnnnnnnnn nnnnnnnnnn nnnnnnnnnn    10071
nnnnnnnnnn nnnnnnnnnn nnnnnnnnnn nnnnnnnnnn nnnnnnnnnn nnnnnnnnnn    10131
nnnnnnnnnn nnnnnnnnnn nnnnnnnnnn nnnnnnnnnn nnnnnnnnnn nnnnnnnnnn    10191
nnnnnnnnnn nnnnnnnnnn nnnnnnnnnn nnnnnnnnnn nnnnnnnnnn nnnnnnnnnn    10251
nnnnnnnnnn nnnnnnnnnn nnnnnnnnnn nnnnnnnnnn nnnnnnnnnn nnnnnnnnnn    10311
nnnnnnnnnn nnnnnnnnnn nnnnnnnnnn nnnnnnnnnn nnnnnnnnnn nnnnnnnnnn    10371
nnnnnnnnnn nnnnnnnnnn nnnnnnnnnn nnnnnnnnnn nnnnnnnnnn nnnnnnnnnn    10431
nnnnnnnnnn nnnnnnnnnn nnnnnnnnnn nnnnnnnnnn nnnnnnnnnn nnnnnnnnnn    10491
nnnnnnnnnn nnnnnnnnnn nnnnnnnnnn nnnnnnnnnn nnnnnnnnnn nnnnnnnnnn    10551
nnnnnnnnnn nnnnnnnnnn nnnnnnnnnn nnnnnnnnnn nnnnnnnnnn nnnnnnnnnn    10611
nnnnnnnnnn nnnnnnnnnn nnnnnnnnnn nnnnnnnnnn nnnnnnnnnn nnnnnnnnnn    10671
nnnnnnnnnn nnnnnnnnnn nnnnnnnnnn nnnnnnnnnn nnnnnnnnnn nnnnnnnnnn    10731
nnnnnnnnnn nnnnnnnnnn nnnnnnnnnn nnnnnnnnnn nnnnnnnnnn nnnnnnnnnn    10791
nnnnnnnnnn nnnnnnnnnn nnnnnnnnnn nnnnnnnnnn nnnnnnnnnn nnnnnnnnnn    10851
nnnnnnnnnn nnnnnnnnnn nnnnnnnnnn nnnnnnnnnn nnnnnnnnnn nnnnnnnnnn    10911
nnnnnnnnnn nnnnnnnnnn nnnnnnnnnn nnnnnnnnnn nnnnnnnnnn nnnnnnnnnn    10971
nnnnnnnnnn nnnnnnnnnn nnnnnnnnnn nnnnnnnnnn nnnnnnnnnn nnnnnnnnnn    11031
nnnnnnnnnn nnnnnnnnnn nnnnnnnnnn nnnnnnnnnn nnnnnnnnnn nnnnnnnnnn    11091
nnnnnnnnnn nnnnnnnnnn nnnnnnnnnn nnnnnnnnnn nnnnnnnnnn nnnnnnnnnn    11151
nnnnnnnnnn nnnnnnnnnn nnnnnnnnnn nnnnnnnnnn nnnnnnnnnn nnnnnnnnnn    11211
nnnnnnnnnn nnnnnnnnnn nnnnnnnnnn nnnnnnnnnn nnnnnnnnnn nnnnnnnnnn    11271
nnnnnnnnnn nnnnnnnnnn nnnnnnnnnn nnnnnnnnnn nnnnnnnnnn nnnnnnnnnn    11331
nnnnnnnnnn nnnnnnnnnn nnnnnnnnnn nnnnnnnnnn nnnnnnnnnn nnnnnnnnnn    11391
nnnnnnnnnn nnnnnnnnnn nnnnnnnnnn nnnnnnnnnn nnnnnnnnnn nnnnnnnnnn    11451
nnnnnnnnnn nnnnnnnnnn nnnnnnnnnn nnnnnnnnnn nnnnnnnnnn nnnnnnnnnn    11511
nnnnnnnnnn nnnnnnnnnn nnnnnnnnnn nnn                                 11544
```